United States Patent [19]
Oppenheimer

[11] Patent Number: 5,331,958
[45] Date of Patent: Jul. 26, 1994

[54] SPECTROPHOTOMETRIC BLOOD ANALYSIS

[75] Inventor: Luis Oppenheimer, Winnipeg, Canada

[73] Assignee: University of Manitoba, Winnipeg, Canada

[21] Appl. No.: 39,583

[22] Filed: Mar. 25, 1993

[30] Foreign Application Priority Data

Mar. 31, 1992 [GB] United Kingdom ............... 9206954
Mar. 31, 1992 [GB] United Kingdom ............... 9206967
Mar. 31, 1992 [GB] United Kingdom ............... 9206970

[51] Int. Cl.⁵ ............................................. A61B 5/00
[52] U.S. Cl. ................................... 128/633; 128/664; 128/665; 356/39
[58] Field of Search ............................ 128/633–635, 128/637, 664–667, 632; 356/39–41

[56] References Cited

U.S. PATENT DOCUMENTS

| H1114 | 12/1992 | Schweitzer et al. ......... 128/633 X |
|---|---|---|
| 3,830,569 | 8/1974 | Meric . |
| 4,243,883 | 1/1981 | Schwarzmann . |
| 4,303,336 | 12/1981 | Cullis . |
| 4,484,135 | 11/1984 | Ishihara et al. . |
| 4,515,165 | 5/1985 | Carroll ........................... 128/664 |
| 4,745,279 | 5/1988 | Karkar et al. . |
| 4,776,340 | 10/1988 | Moran et al. . |
| 4,819,752 | 4/1989 | Zelin ............................... 128/664 X |
| 5,048,524 | 9/1991 | Bailey . |
| 5,066,859 | 11/1991 | Karkar et al. . |
| 5,149,503 | 9/1992 | Kohno et al. . |
| 5,190,040 | 3/1993 | Aoyagi ........................... 128/633 |
| 5,195,963 | 3/1993 | Yafuso et al. ................. 128/633 |

OTHER PUBLICATIONS

Lanken et al, *J. Appl. Physiol.*, 59(2): 580 (1985).
Oppenheimer et al, *J. Appl. Physiol.*, 62(1): 364 (1987).
Oppenheimer et al, *J. Appl. Physiol.*, 69(2): 456 (1990).
Landolfo et al, Abstract, *Am Rev. Resp. Dis.* 141: A296 (1990).
Palomar, Smit & Oppenheimer, Abstract (Apr. 1992).
Smit, Palomer & Oppenheimer, Abstract (Apr. 1992).
Palomar, Light, Bell, Smit & Oppenheimer, Abstract (May 1992).

Primary Examiner—Angela D. Sykes
Attorney, Agent, or Firm—Timothy R. Kroboth

[57] ABSTRACT

A method and device are described which are particularly useful for continuous on-line monitoring of hematocrit and other blood parameters. The effect of change in blood electrolyte composition, for example, in blood sodium concentration, is taken into consideration. This effect has been found to change light beam geometry, and is taken advantage of to provide for blood sodium concentration measurement. The devices may be applied to extracorporeal circuits or to body parts capable of being transilluminated. The devices may be used to optimize dialysis, and also for monitoring optically detectable, exogenous macromolecules.

21 Claims, 12 Drawing Sheets

INCREASING SODIUM

SODIUM EFFECT
940 nm

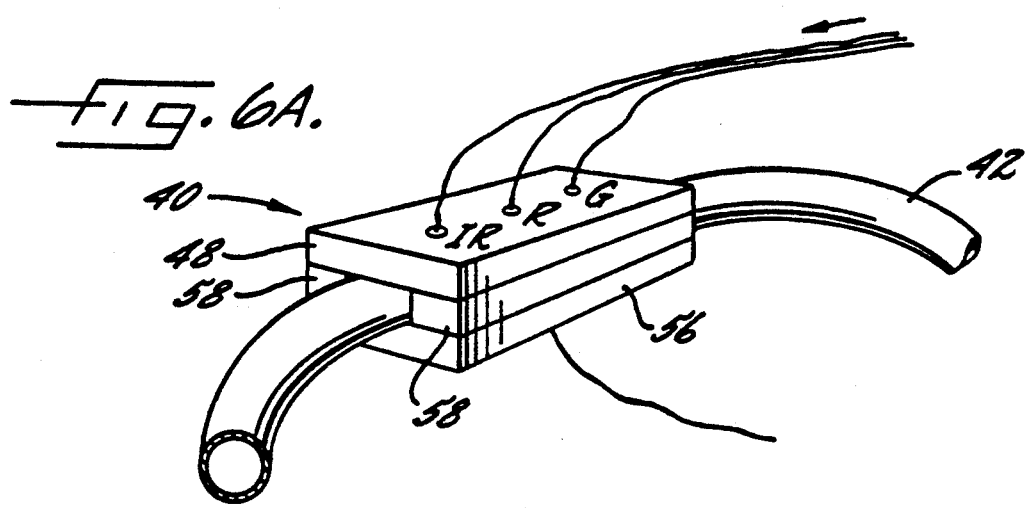
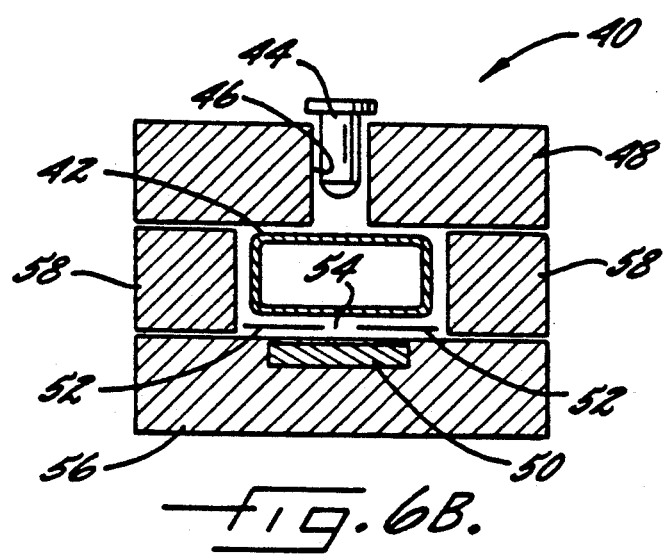
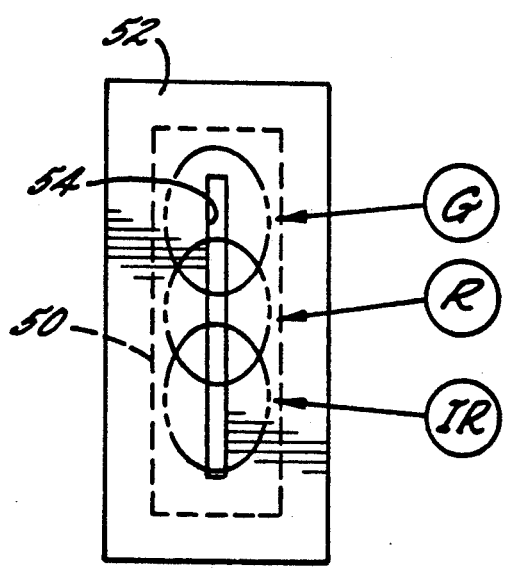

SPECTROPHOTOMETRIC BLOOD ANALYSIS

BACKGROUND OF THE INVENTION

This invention relates to the spectrophotometric analysis of blood parameters.

Blood parameters or indices such as hematocrit and transvascular fluid exchange, provide important clinical information. For example, there are a number of clinical conditions, e.g. renal failure and massive fluid overload, which require fluid removal by natural means or the use of artificial devices, and in which it would be beneficial to be able to achieve an optimal rate of fluid removal.

Commonly used clinical approaches for fluid removal include an extracorporeal circuit. Because the body tissues and the blood stream are in direct communication, fluid removal from the blood results in an imbalance of forces which favors fluid movement from the tissues toward the blood stream. Continuous fluid removal from the blood stream therefore results in continuous mobilization from the tissues, which is the ultimate purpose of the therapy.

However, if fluid removal from the blood stream is induced at a rate faster than fluid can be mobilized from the tissues, patients can become hypotensive (shock). This complication is difficult to predict even if blood pressure is followed continuously. Presumably, hemodynamic compensatory mechanisms succeed in maintaining normal blood pressure even in the presence of hypovolemia until decompensation ensues and circulatory shock develops. To prevent this possibility, fluid removal may be induced at a very slow rate; however, this approach is disadvantageous. It is therefore desirable to achieve an optimal rate of fluid removal: the fastest rate possible without inducing hypotension. In this way, dialysis may be optimized.

Fluid removal from the blood or fluid mobilization from the tissues into the blood results in change in the hematocrit, the fraction of red cell volume relative to total blood. Change in hematocrit induces change in the optical properties of blood.

Because red cells contain hemoglobin, a naturally occurring pigment with a continuous spectrum of light absorption throughout the ultraviolet, visible, and infrared ranges, changes in hematocrit result in changes in blood hemoglobin concentration and therefore in changes in light transmission across a blood column. It has been established that hematocrit may be correlated with light transmission changes across a flowing blood column, and measurements of hematocrit may be used to derive measurements of other blood indices.

As illustrated by U.S. Pat. Nos. 3,830,569 to Meric, 4,243,883 to Schwartzmann and 4,303,336 to Cullis, a spectrophotometric device for measuring blood indices including a suitable light source and photodetector is known. The light source may be a laser with a collimating lens mounted in front of the laser, and the light source may be remote from or proximate to the blood. As shown by Meric, multiple detectors in combination with a centrally disposed, light trap have been used, and a shield provided with windows may be disposed in the light path.

Also known as exemplified by U.S. Pat. No. 4,484,135 to Ishibara et al, is hematocrit determination by blood resistivity measurement. This patent criticizes measurements deriving hematocrit from blood cell count and mean blood cell volume, for using diluted blood if the concentration of the electrolyte and protein in the diluted blood has been changed.

As illustrated by J. Appl. Physiol., 62(1): 364 (1987), light transmissive, plastic tubing through which blood is circulated, may be placed between light sources and light detectors disposed generally opposite from the light sources. High molecular weight, Blue Dextran may be used as an impermeable, reference tracer. As exemplified by J. Appl. Physiol., 69(2): 456 (1990), to ensure detection of a widely scattered light beam, detectors connected in parallel to a photodetector circuit may be used. A separate detector may measure light fluctuations. Diluted perfusate is described.

Unless taken into account, measurement artifacts may induce error in determining blood parameters from optical properties of the blood. One well-known artifact results from changes in the degree of oxygen saturation of hemoglobin ($SaO_2$). It has been found that this artifact may be avoided by selecting a specific wavelength or isobestic point at which the hemoglobin oxygen content does not influence light transmission. Isobestic points are known in the IR range (approximately 814 nm), in the green range (approximately 585 and 555 nm), and in the UV range.

As illustrated by U.S. Pat. Nos. 4,745,279 to Karkar et al, 4,776,340 to Moran et al, 5,048,524 to Bailey, and 5,066,859 to Karkar et al, additional detectors have been used to compensate for various measurement artifacts, in particular for variation in intensity of light entering the blood stream. In Karkar '279, a detector for diffused light is used in combination with a compensating detector directly illuminated by another light source. In Moran, a far detector and a near detector are used, and the ratio of the separately amplified signals is determined. Similar to Moran is U.S. Pat. No. 5,149,503 to Kohno et al, in which an additional emitter location and signal ratios are used.

In Karkar '859, a pair of far field detectors for determining hematocrit and a pair of near field detectors for obtaining oxygen saturation measurements are used. The far field detectors are spaced equidistant from a light emitting fiber, and one of the far field detectors is used to compensate for the signal detected by its paired fiber.

However, the correlation between blood parameters and optical properties of blood needs to be improved. Accordingly, there is a need for improvement in using the optical properties of blood to determine blood indices. Beneficially, applications relating to monitoring of bodily fluid shifts would be facilitated. For instance, monitoring of fluid removal, including as appropriate the use of feedback, so as to achieve an optimal rate of removal, would be facilitated. In connection therewith, drug therapy for, for instance, inducing fluid reabsorption or restoring vascular membrane permeability may be used.

SUMMARY OF THE INVENTION

In accordance with the purpose of the present invention, as embodied and broadly described herein, there is provided a novel method for optically determining blood parameters. In accordance with the method, a light beam is directed into a patient's blood and light emerging from the blood is detected taking into consideration the effect of change in light scatter resulting from for example, change in blood electrolyte composition. Typically, an isobestic wavelength may be used, in which case a single wavelength may be sufficient to determine hematocrit and blood sodium concentration. Related blood values may be determined from hematocrit.

In a variation when an isobestic wavelength is used, light of a second wavelength, or of even additional wavelengths, may be directed into the patient's blood. In this way, other blood parameters such as blood concentration of exogenous, optically detectable macromolecules, may be optically determined. Accordingly, the term "blood parameter" as used in this description of the present invention, includes blood concentration not only of endogenous macromolecules such as hemoglobin but also of exogenous macromolecules.

In accordance with the present invention, fluid balance may be monitored and used for fluid management. Moreover, the information obtained by monitoring fluid balance, may be used to regulate the rate of fluid removal. Drug therapy in conjunction with fluid removal, may be used to, for instance, induce fluid reabsorption or restore vascular membrane permeability.

Also provided is a novel device for optically determining blood parameters. The device comprises means for generating a light beam to be directed into a patient's blood; means for detecting light emerging from the blood taking into account the effect of change in light scatter; and signal evaluation means in operative communication with the light detecting means. Beneficially, the device may be used with an extracorporeal circuit through which blood flows, to continuously or intermittently monitor a patient for selected blood parameters.

In the drawing and in the detailed description of the invention that follows, there are shown and essentially described only preferred embodiments of this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWING

Reference is now made to the accompanying drawing, which forms a part of the specification of the present invention.

FIGS. 6A-6C illustrate a comparative monitoring device, with FIG. 6B being a cross-sectional view;

DETAILED DESCRIPTION OF THE INVENTION

As mentioned, change in hematocrit induces change in the optical properties of blood. It has now been discovered that factors that influence change in light scatter should also be taken into account in determining blood parameters from optical properties of blood. By comparison, the technique described in *J. Appl. Physiol.*, 69(2): 456 (1990), attempts merely to ensure detection of the scattered light beam and hence maximize the signal.

It has previously been observed that equivalent volumes of 0.9% NaCl (Normal Saline) and plasma produce significantly different changes in light transmission across a flowing blood column, although the expected hematocrit change would be the same. It has now been discovered that this phenomenon may be corrected for by taking into account the effect of change in blood electrolyte composition, in particular blood sodium concentration.

Figure 1:
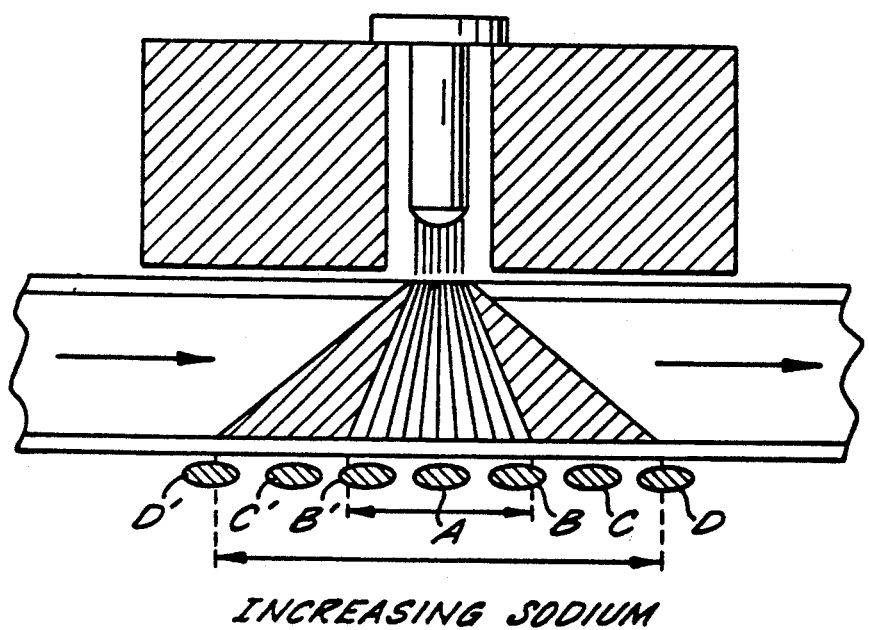
FIG. 1 illustrates the effect of change in sodium concentration on light beam geometry.

This phenomenon, conveniently referred to as the "scatter effect" (or "sodium effect" when change in blood sodium concentration is involved), is illustrated in FIG. 1. As indicated in the Figure, changes in signal proportional to incident light resulting from changes in blood sodium concentration, may be evaluated using a series of photodiodes placed at 5 mm intervals across from a discrete light source, and by separately amplifying the signal from each photodiode. As shown, incident light is significantly scattered by a red cell suspension so that a significant fraction (scattered fraction) is no longer generally perpendicular when it reaches the detector side. The proportion of scatter is directly proportional to the sodium concentration. In other words, as the blood sodium concentration increases, the degree of scatter increases; whereas, as blood sodium concentration decreases, the degree of scatter decreases.

This phenomenon influences not only the fraction of light which reaches a detecting surface, but also the average angle, and hence the current generated by a photodetector for any given incident light. Using a constant light source output, a widening of the light scattering angle, as shown in FIG. 1, results in a decrease in incident light per surface area, and thus output from detectors previously receiving light decreases. However, the wider beam now reaches detectors further away from the light source. Similarly, as indicated in FIG. 1, when at the outset of measurement, the beam impinges upon outermost detectors C,D, and blood sodium concentration decreases, then the outermost detectors will sense a decrease in incident light and centermost detectors A,B will sense an increase in incident light.

According to the present invention, this understanding of induced change in light scatter and change in output signals of detectors in response to change in light scatter, is beneficially used in the determination of blood parameters from optical properties of blood, including determination of blood sodium concentration. It may be that light scatter is affected by the relationship of the diameter of red cells to the wavelength of the emitted light, and that the diameter of red cells varies as the concentration of small ions such as sodium varies because of osmotic effect on red cells.

Consequently, signal changes may reflect not only change in hematocrit (and fluid exchange in or out of the intravascular space), but also change in the electrolyte composition of plasma. This phenomenon is further illustrated in FIG. 2, in which changes in signal expressed in LOG(VOLT), are plotted against changes in hematocrit for a 10% dilution with plasma, normal saline (NS) and water. It will be understood that change in signal could alternatively have been expressed in for example, change in percent transmittance, optical density or absorbance.

Figure 2:
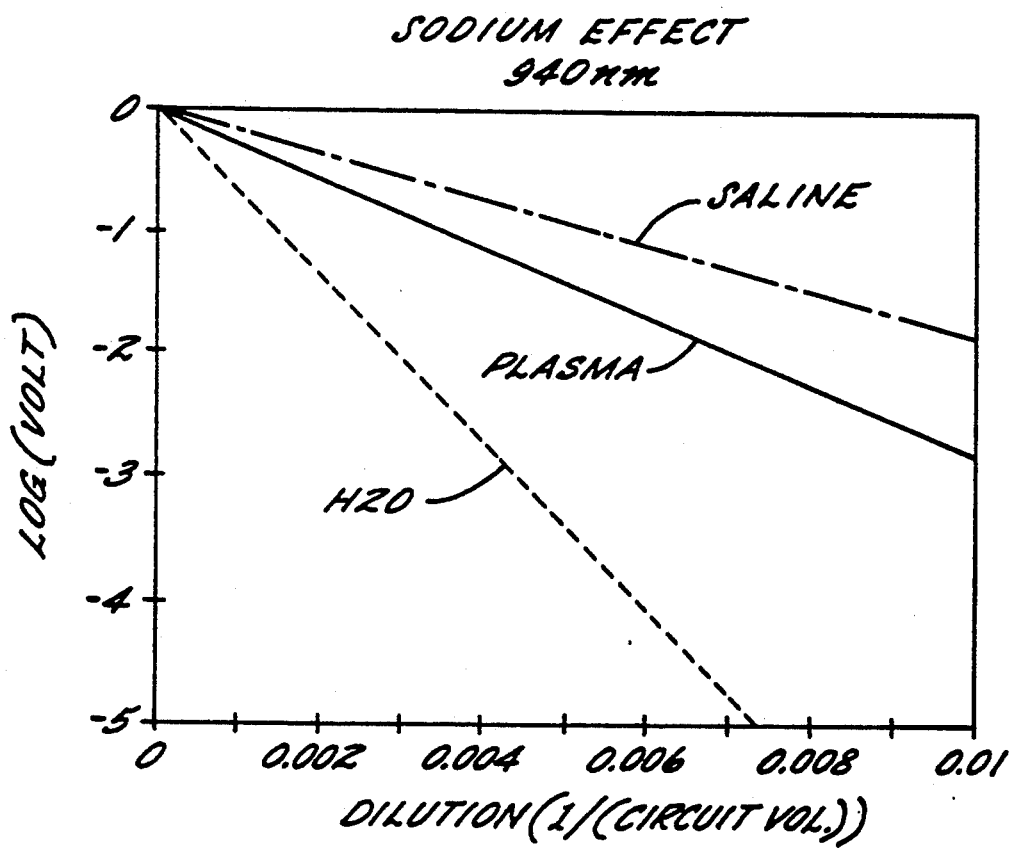
FIG. 2 shows the effect of 10% dilution with plasma, normal saline and water.

The solid line in FIG. 2 represents addition of plasma (isoionic). The dashed and dotted lines represent changes induced by the addition of normal saline (about a 3 mEqu/L total Na increase) and water (about a 10 mEqu/L total Na decrease), and show that an equivalent dilution accompanied by increased sodium concentration, decreases the signal and signal change compared to plasma, and that an equivalent dilution accompanied by decreased sodium concentration (water addition), increases the signal and signal change compared to plasma. The sodium effect not only significantly influences estimates of volume exchange, but also estimates of $SaO_2$ and saturation related correction factors.

Figure 3:
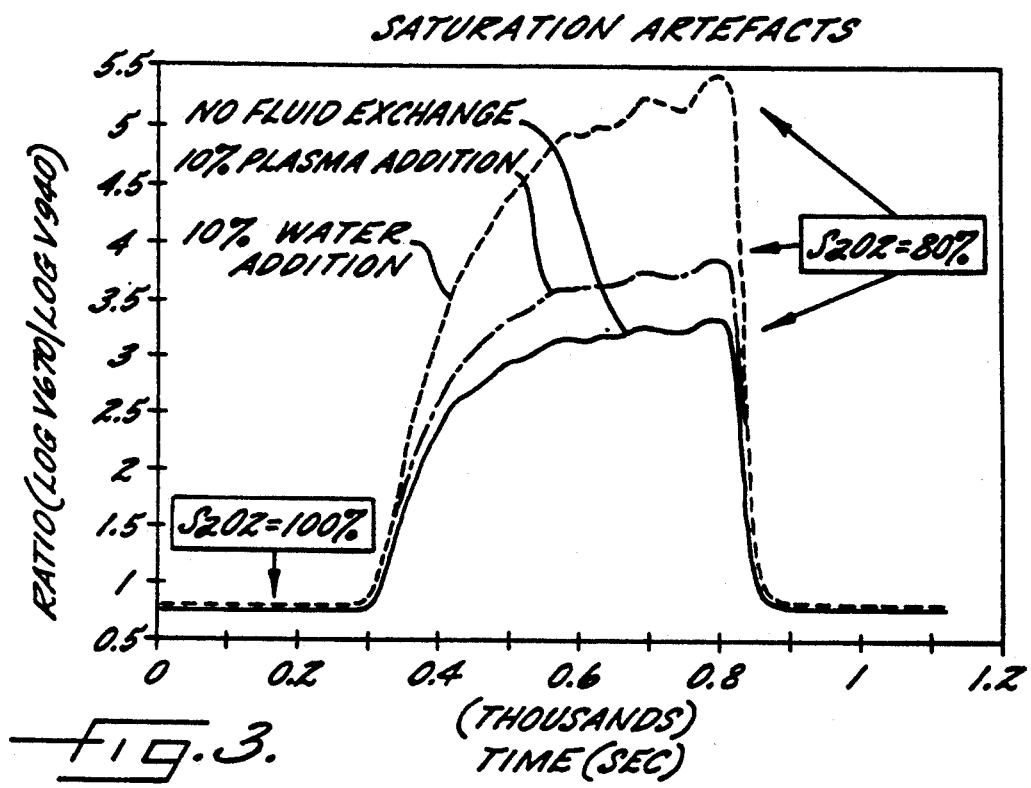
FIG. 3 shows the effect of change in oxygen saturation and the effect of sodium concentration change, on the ratio of 670/940 nm Absorbance.

In FIG. 3, the effect of change in oxygen saturation and the effect of change in sodium concentration on the ratio of 670/940 nm Absorbance, is shown. The effects of addition of plasma (dashed line, isoionic) and an equivalent volume of water (dotted line, 8 mEqu/L Na decrease) are added to pure changes in $SaO_2$ (solid line). These significant errors are predominantly the result of dilution and sodium effects on 940 nm light transmission, which is much less affected by $SaO_2$ changes than 670 nm light.

Changes in blood flow also induce changes in light scatter, and thus may be advantageously taken into account when the optical properties of a flowing blood column are analyzed. The axial distribution of red cells in a flowing column is related to linear velocity. Changes in blood flow would change the distribution of red cells in the column.

Using the same approach as described in connection with FIG. 1 (multiple detectors arranged in the direction of flow), changes in blood flow may be evaluated, and may be seen to produce inverse effects on detectors located immediately across, compared to a further distance away, from a constant light source. Thus, changes in flow produce a scatter effect like that of changes in blood electrolyte composition. In other words, increased flow produces a change in light scatter in the same way as increased sodium, and decreased flow has a similar effect to decreased sodium.

Figure 4:
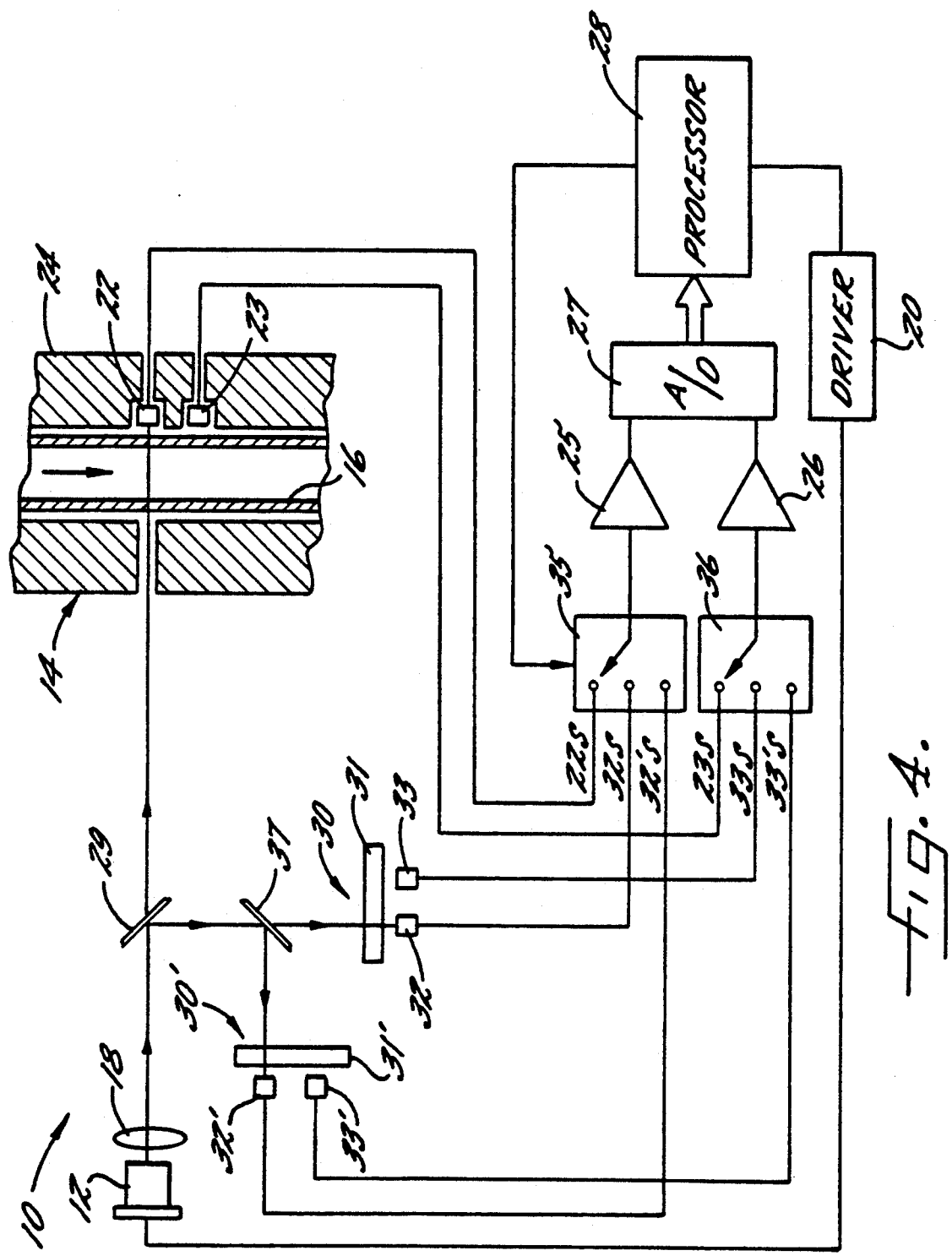
FIG. 4 illustrates a preferred embodiment of a device in accordance with the present invention.

In accordance with the present invention and taking into account the change in output signals of detectors in response to change in light scatter, a device 10 is provided in the preferred embodiment shown in FIG. 4. Beneficially, there is no need to carry out prior to analysis, artificial intervention by which a patient's blood is diluted or, as described in U.S. Pat. No. 3,830,569 to Meric, the red cells are spherized. As a result, the present invention may be applied to the flowing blood of a patient either in an extracorporeal circuit or in a body part that can be transilluminated, without any detrimental effect on the blood or the patient's health.

With reference to FIG. 4, the device includes means 12 for generating a light beam to be directed into a patient's blood. Suitably, light source 12 may be disposed remote from a housing 14 provided with a channel for receiving light transmissive tubing 16 of, or a light transmissive flow cell inserted into, an extracorporeal circuit. Fiber optic cable carrying specific light, may be used. Alternatively, the light source may be disposed in an opening in the housing.

Conveniently, to avoid $SaO_2$ correction, a light source that emits an isobestic wavelength, may be used. An advantageous light source is a laserdiode, and a useful isobestic wavelength may be in the IR range. Beneficially, light scatter is increased when IR light is used, compared to for example red or green light; as a result, resolution and sensitivity may be improved.

When the light source is a laserdiode, a collimating lens 18 is typically disposed in the light beam path. A conventional driver 20 for the light source may be used.

Figure 5:
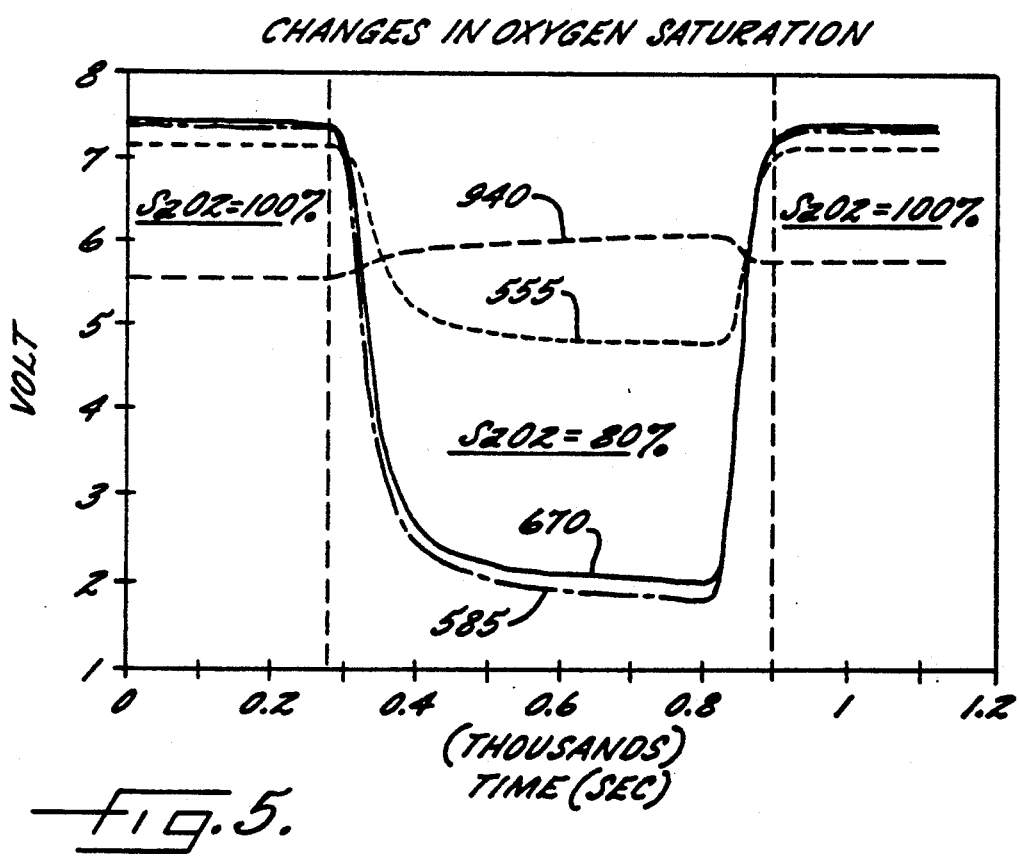
FIG. 5 shows the sensitivity of different wavelengths to change in oxygen saturation.

Alternative light sources may include LEDs. However, LEDs are disadvantageously sensitive to $SaO_2$ changes. See FIG. 5 in which changes in signal are compared using LEDs rated at 555 and 585 nm, isobestic wavelengths in the green range, when $SaO_2$ is decreased from 100 to 80%. Included in the Figure are data for LEDs rated at 670 and 940 nm. The 670 nm wavelength is commonly used to monitor changes in $SaO_2$ clinically. Note that signal changes for 940 nm light occur in the opposite direction. When multiple light sources are used, the $SaO_2$ effect may be eliminated by mathematical correction.

Presumably, even though rated (average wavelength) at an isobestic point, LEDs emit too many other wavelengths affected by oxygenation. Thus, the wavelength of any given light source (incandescent, laser, laserdiode or LED), in continuous or pulsed wave modes must coincide precisely with that of the selected isobestic point to avoid correcting for the $SaO_2$ effect. Like laserdiodes, lasers beneficially emit virtually a single wavelength. Incandescent light sources directed across narrow band width interference filters, may be used.

In accordance with the present invention, device 10 further includes detector means for detecting light emerging from the blood. Conventional photodiodes may be used. An important aspect of the present invention is that light detector means 22,23 are disposed at locations suitable for sensitivity to change in scatter of the light emanating from light source 12, and are diposed at different locations with respect to the light beam.

A further significant feature is that light detection means 22 is located so as to predominantly detect change associated with directly emerging light, that is, with light that maintains a generally straight-line path through the blood. To this end, as applied to transmitted light as shown in FIG. 4, detector 22 is directly illuminated by the light source, and may be beneficially located in the center of the light beam, that is, in line with the optical axis, for enhanced sensitivity. Advantageously, in the case of through detector 22, the blood path length of directly transmitted light, is typically about 3 mm or more.

Suitably, dimensions for detectors 22,23 may be about 4 mm×5 mm, and the detectors may be spaced apart, center to center, a distance of about 13 mm. For convenience, detector 23 may be termed a "scatter detector". Detectors 22,23 are located proximate to one another, conveniently in a detector cover 24 of housing 14.

In accordance with the present invention, device 10 further includes signal amplification means. Conventional operational amplifiers may be used. Advantageously, a first amplification means 25 operatively communicates with through detector 22, and a second amplification means 26 operatively communicates with scatter detector 23. As a result, detected signals from electronically discrete locations are separately amplified.

Also in accordance with the present invention, the device advantageously includes conventional analog to digital converter means 27, and signal processing means 28. Beneficially, amplification means 26 may provide a greater degree of amplification than amplification means 25 so that a relatively weaker signal from detector 23 may be brought up to about the range of the signal from detector 22 for A/D conversion.

A conventional microprocessor may be used as the signal processing means. Means 28 operatively communicates with, and, as explained in further detail below, serves to separately evaluate the signals received from, amplification means 25,26.

With continued reference to FIG. 4, the emitted light may be advantageously split by a conventional light splitting element 29 so as to be partially directed toward a reference unit 30, conveniently remotely disposed from the portion of the light beam directed into the primary detection unit ("primary light beam"). The term "remotely" is used to make it clear that the reference unit is not, like detector 23, proximate to detector 22 or the primary light beam.

Reference unit 30 includes a slot 31 for inserting known standards, and light detector means 32,33, conveniently located in like manner with respect to the portion of the light beam directed toward the reference unit, as detectors 22,23 are located with respect to the primary light beam. As may be understood, a reference unit may be advantageously used when the present invention is applied to continuous or intermittent determination of blood parameters from flowing blood, for the reason that extracorporeal circuit tubing occupies housing 14. The patient's blood may be used as a calibrating reference.

Signals from detectors 32,33 are beneficially processed in like manner as the respective signals from detectors 22,23. To so provide, switch means 35,36 respectively control signal feed 22S,32S from detectors 22,32 and signal feed 23S,33S from detectors 23,33 to the respective amplifiers. Conventional analog switches may be used as the switch means, and the analog switches may be beneficially controlled by microprocessor 28.

Similarly, with continued reference to FIG. 4, the split light beam may be further split by a second conventional light splitting element 37 so as to be partially directed toward an additional reference unit 30'. Reference unit 30' includes a slot 31' for inserting known standards, and light detector means 32',33'. These detectors are conveniently located in like manner with respect to the portion of the light beam directed toward the reference unit, as detectors 22,23 are located with respect to the primary light beam.

Signals from detectors 32',33' are beneficially processed in like manner as the respective signals from detectors 22,23. To so provide, switch means 35,36 respectively control signal feed 32'S from detector 32' and signal feed 33'S from detector 33' to the respective amplifiers.

As may be understood, multiple standards or references may be beneficially used for calibrating, and to avoid operator replacement or substitution thereof, reference unit 30' may be advantageously used. Thus, a simpler device may be provided that requires more operator responsibility, and that omits reference unit 30'. However, a further benefit of reference unit 30' is repeated, calibration readings under the control of microprocessor 28.

As explained in further detail below, means 28 separately processes the separately amplified reference signals and compares these signals with the separately amplified signals from detectors 22,23, and based thereon, provides corrected signal information. Means 28 may further function to use the signal information to perform calculations to determine blood parameters. As indicated, means 28 advantageously controls the emission of light by light source 12.

In accordance with the present invention, a method for determining blood parameters from optical properties of blood, is provided. By the method, a light beam is directed into a patient's blood using a light source as previously described, and light emerging from the blood is detected.

As applied to transmitted light, the primary detection unit may consist of through detector 22, and at an electronically discrete location suitable for sensitivity to change in light scatter, detector 23; however, other elements or procedures useful for providing signals capable of enabling change in light scatter to be taken into account, may be used. In any event, the signals are separately amplified. Thereafter, the amplified signals are separately evaluated with respect to separately amplified reference signals, to provide a corrected signal.

As explained, the present invention takes into account the effect of change in blood electrolyte composition, in particular blood sodium concentration, on light scatter. Thus, in a preferred embodiment of the present invention, standards providing for known hematocrit and sodium values are used, and reference signals are beneficially used to determine a reference line or line slope for hematocrit and a reference line or line slope for sodium. Raw hematocrit and sodium values determined from the signals from the main detector unit, may then be compared to the reference readings to determine the absolute hematocrit and sodium values of the patient's blood. Accordingly, by use of the present invention, hematocrit, related blood parameters, and blood sodium concentration may be determined. Moreover, by at a subsequent point in time, inputting signal information from the main detector unit into the microprocessor, change in hematocrit, related blood parameters, and blood sodium concentration may be obtained by comparison with information previously processed and stored in memory.

Processing of signal information to determine raw hematocrit and sodium values may be by the use of the following equations:

$$S = HE_s + NAE_s$$

$$T = HE_t + NAE_t$$

where S is the signal from the scatter detector, $HE_s$ is the portion of the scatter detector signal attributable to hematocrit, $NAE_s$ is the portion of the scatter detector signal attributable to the sodium effect, T is the signal from the through detector, $HE_t$ is the portion of the through detector signal attributable to the hematocrit, and $NAE_t$ is the portion of the through detector signal attributable to the sodium effect.

Referring again to FIG. 1, more than two electronically discrete, detecting means may be advantageously used. If only detectors A,C were present and the light beam became more focused as a result of decreasing sodium concentration, only detector A would sense a change in impinging light. However, as previously indicated, the present invention is based on taking into account change in output signals of detectors, whereas there is no change in output signal of detector C. As may be understood, the problem is that in this case, detector C is not suitably located for sensitivity to change in light scatter, whereas detector B is so located. In a highly preferred embodiment of the present invention, the signal evaluating means may preliminarily determine the beam geometry, in particular the location of the beam edge, and based on this determination, may select appropriate detectors for signal evaluation.

Because dialysis and CAVH (continuous arteriovenous hemofiltration) require an extracorporeal circuit, device 10 may be used to continuously or intermittently monitor blood parameters by measuring light transmission changes across the circuit tubing or a flow cell inserted into the circuit. By monitoring hematocrit, the rate of ultrafiltration may be optimized by providing for the maximum rate of fluid removal which will not result in a sustained or excessive increase in hematocrit, that is, the maximal rate of fluid removal which can be matched safely by fluid mobilization from the tissues into the blood stream.

The on-line, monitoring devices now described are used in connection with an extracorporeal circuit through which a patient's blood is circulated. However, as may be understood by one skilled in the art, the inventive concept is equally applicable to analysis of blood in a body part that can be transilluminated.

A comparative monitoring device 40 is depicted in FIG. 6. Made of opaque plastic, the device may be directly applied over light transmissive, circuit tubing 42. Device 40 uses light sources 44 (one shown in FIG. 6B) that emit wavelengths, one greater than 814 nm and two smaller than 814 nm. For example, the following wavelengths generated by LEDs may be used: 940 nm (IR), 670 nm (red) and 555 nm (green), indicated in the FIG. 6 as IR, R and G, respectively.

With particular reference to FIG. 6B, each LED may be disposed in a cylindrical opening 46 in a cover 48 of the opaque plastic housing. The cylindrical openings serve to collimate the light beams. A single, rectangular, large surface photodiode 50, covered by a conventional light blocking member 52 except for a longitudinal slit 54 aligned with the direction of flow, is disposed generally opposite the light sources in a detector cover 56. Covering a detector surface except for such a slit may be useful in minimizing the effect of change in blood flow. As covers 48 and 56, separated by spacers 58 are clamped together, tubing 42 is made to conform to an appropriate geometry having beneficially flatter surfaces, and the tubing is located adjacent the detector surface.

To prevent leakage of ambient light through the tubing walls, black tape may be wrapped around the tubing to block approximately 7 cm on each side of the device. Alternatively, a short piece of flexible or rigid plastic tubing, long enough to fit into the device and provided with opaque connectors could prevent light leakage.

Microprocessor analysis of pulsed signals represents an additional alternative for ambient change corrections. More precisely, the DC/AC ratio of pulsed signals may be used to correct for ambient, background changes related to temperature and light leakage.

The LEDs are pulsed sequentially using very stable current supplies. The areas illuminated by the three wavelengths are represented in FIG. 6C with dashed ellipses, which include transmitted and scattered light for each pulsed wavelength. The photodetector signal, proportional to incident light, is amplified, digitized, decoded and used for the following corrections using a microprocessor, the signal being expressed as log(Volt):

Correction for $SaO_2$

Figure 7:
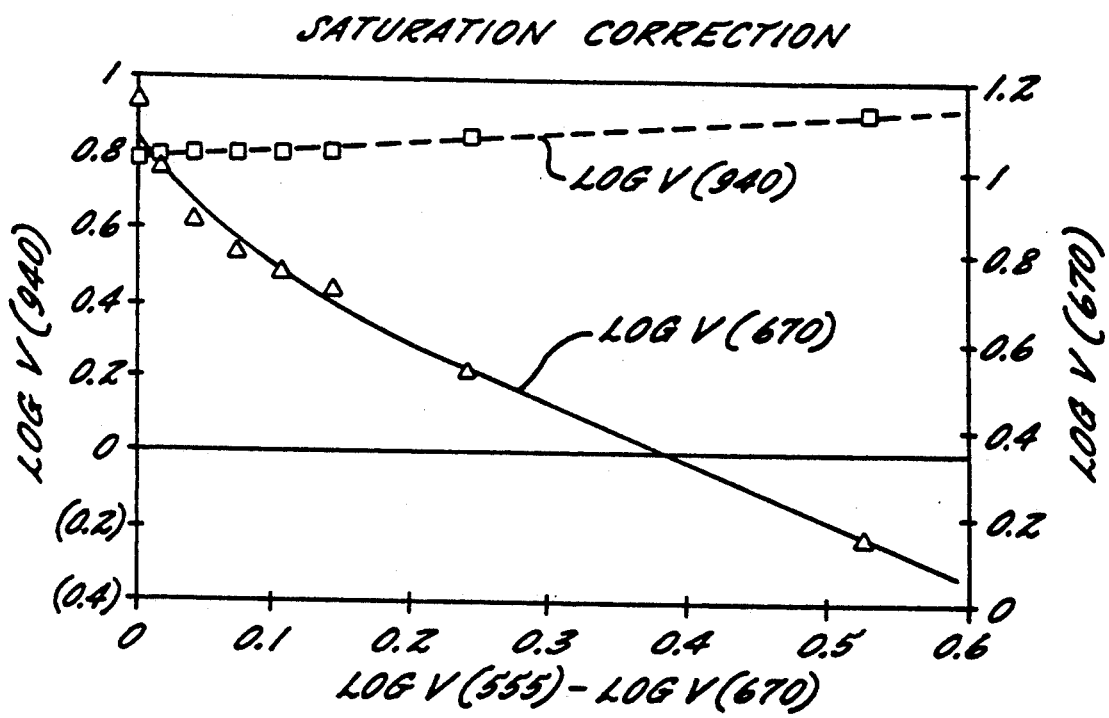
FIG. 7 illustrates a graph correcting for change in oxygen saturation.

When using wavelengths <814 nm, for example, 555 and 670 nm, changes in signal related to hematocrit, sodium effect and flow changes are identical. Therefore, the difference between these two signals is proportional exclusively to changes in $SaO_2$ (all other effects are eliminated by the subtraction). In FIG. 7, this difference is plotted against changes in 670 nm and a wavelength >814 nm, for example 940 nm light, to correct these signals for saturation related changes.

Correction for Scatter Effect

Signals from wavelengths higher and lower than 814 nm, for example 940 and 670 nm signals, respond almost identically to flow changes. Although there is a difference in response to the sodium effect, the difference between the two signals (after $SaO_2$ correction) reflects, predominantly changes in hematocrit. With this approach, although not totally abolished, error resulting from change in light scatter is substantially decreased.

The device of FIG. 6 uses a single detector and pulsed signals. To avoid the use of pulsed signals, each wavelength may be followed by a separate detector; however, enough separation between detectors must be provided to avoid detrimental "cross-talk".

PREFERRED DEVICE #1

Figure 8:
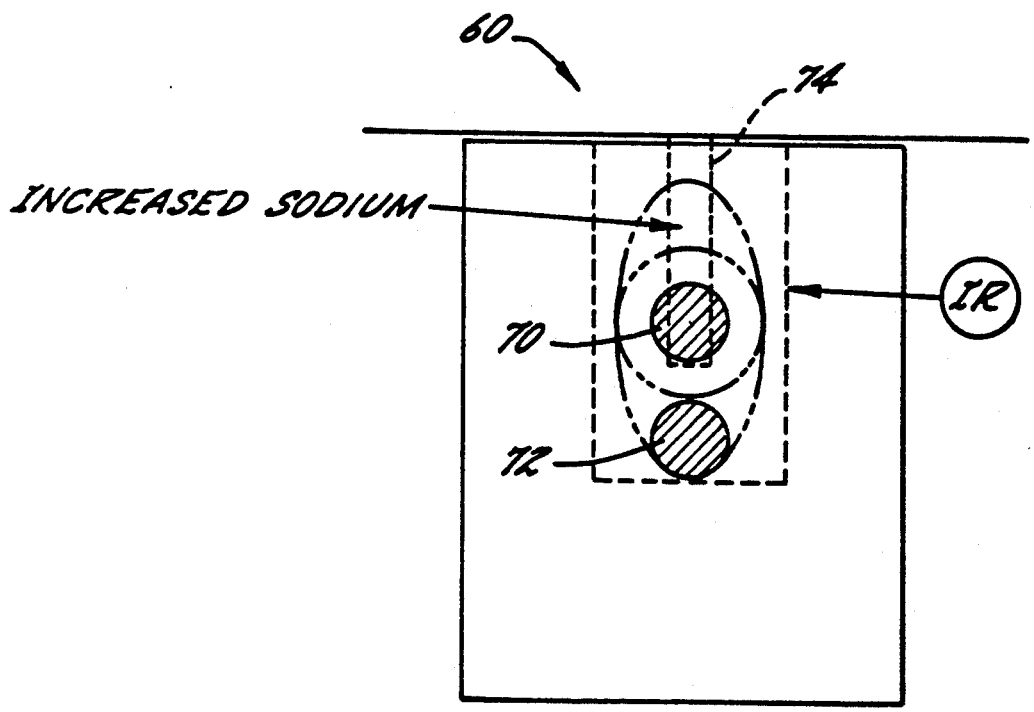
FIG. 8 illustrates a preferred embodiment of a device, partial view, in accordance with the present invention.

This monitoring device is a modification of the device of FIG. 6, by which the scatter effect is taken into consideration. FIG. 8 shows the manner in which infrared (IR) portion of the detector component of the device of FIG. 6 may be modified to provide preferred device 60. No other change is required. This preferred device provides a more accurate determination of hematocrit and related blood indices, and beneficially a determination of blood electrolyte composition, for instance, blood sodium concentration.

The $SaO_2$ correction is performed as described for the device of FIG. 6. As now described, changes in hematocrit are computed from a signal >814 nm, in this case, from changes in the 940 nm signal.

With reference to FIG. 8, to take into account change in light scatter, two small photodiodes 70,72 are disposed generally opposite the 940 nm light source. The dotted circle represents the beam geometry of transmitted light emanating from the 940 mn light source with normal sodium concentration. One photodiode (detector 70) is placed directly in line with the light source or light beam, to predominantly detect changes associated with directly transmitted light. The other photodiode (detector 72) is placed a distance away suitable for sensitivity to change in the scatter of transmitted light emanating from the 940 nm light source. The dashed ellipse represents widened beam geometry due to increased sodium concentration. As may be understood, detector 72 may be located in any position relative to the beam edge, for instance, just outside or within the beam edge, that provides for sensitivity to change in the light scatter.

Alternatively, detector 74 (shown in part), which is common to the green and red light sources, may be extended to assume the function of through detector 70. Accordingly, this monitoring device may use three separate detectors (common detector 74 and IR detectors 70,72), or two separate detectors (common detector 74, which assumes the function of through detector 70; and detector 72).

Figure 9A:
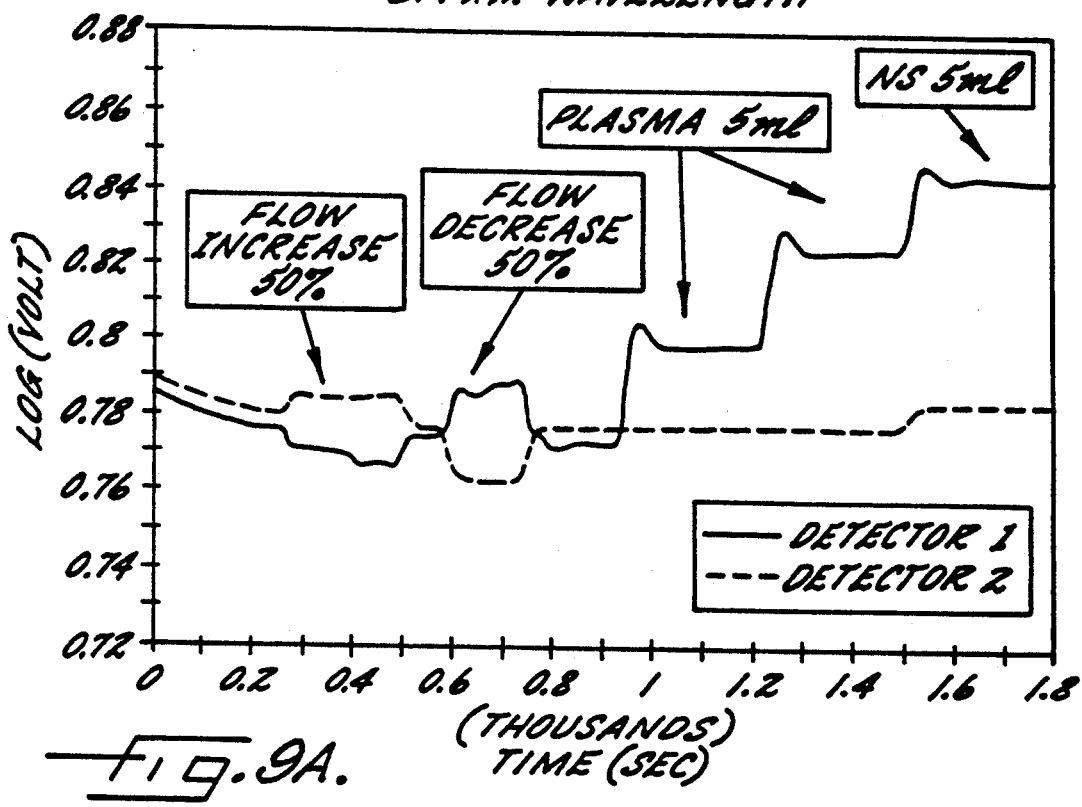
FIGS. 9A-9B show corrections for change in sodium concentration and flow, in connection with the device of FIG. 8.
Figure 9B:
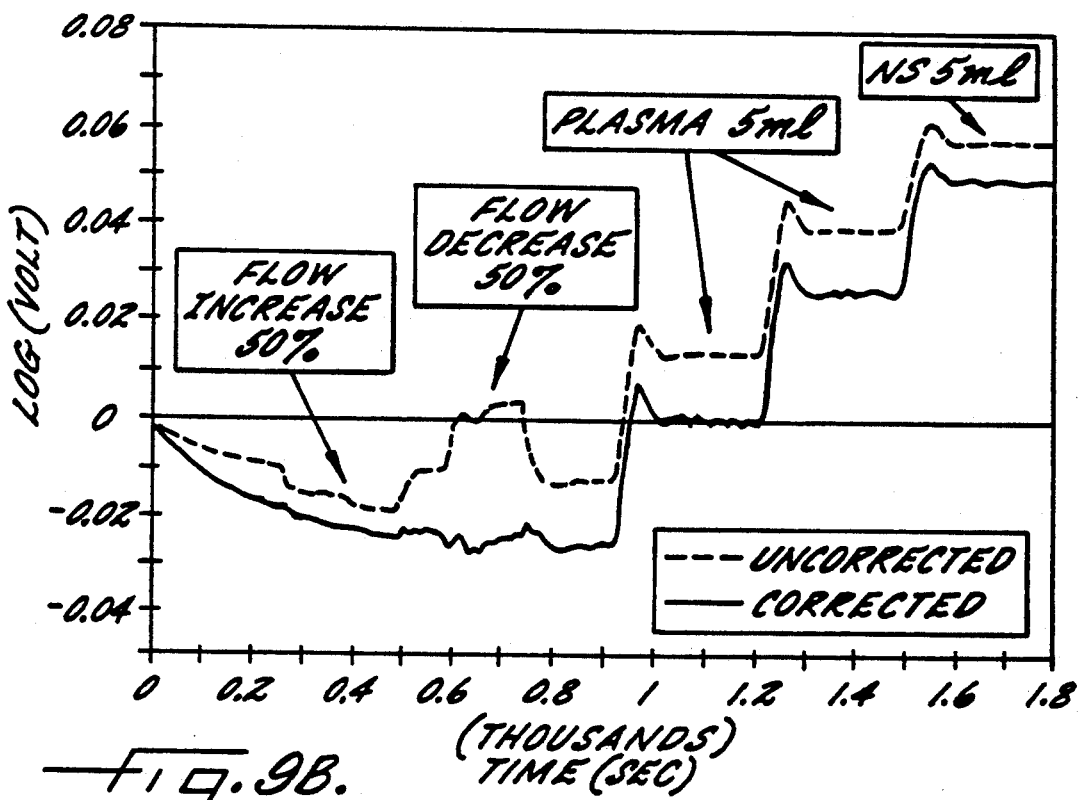

As shown in the upper panel of FIG. 9, which summarizes the signals from detectors 70,72, changes in blood flow through the device of FIG. 8, move in opposite directions when signals from detectors 70,72 (indicated as detectors 1 and 2, respectively) are compared. Also as shown in the upper panel, isoionic changes in hematocrit (PLASMA 5 ml addition, FIG. 9) affect the detector 1 signal but do not affect the detector 2 signal. As shown in FIG. 8, detector 2 is just outside the beam edge, and with an isoionic change, there is no change in the beam geometry (dotted circle). Note the detector 1 signal increases in response to a decrease in the ratio of red cells to fluid. Similarly, a decrease in the ratio of red cells to fluid produces a decrease in the detector 1 signal. As may be understood, when detector 2 is disposed to be within the beam edge (dotted circle, FIG. 8), the detector 2 signal would be affected by an isoionic change, and in the same direction as the detector 1 signal.

However, as shown in the upper panel, a blood electrolyte change, in particular an increase in sodium (NS 5 ml addition, FIG. 9; light beam geometry now represented by dashed ellipse, FIG. 8), affects both the detector 1 and detector 2 signals. Note from the upper panel that both detector signals increase, but that similar to FIG. 2 (solid and dashed lines) the extent of change in the detector 1 signal is less than for the isoionic change in hematocrit. As may be understood, the decreased extent of change in the detector 1 signal results from the change in light beam geometry due to the sodium effect. Therefore, to take into account the sodium effect, that is, the change in light scatter, so as to have a correct signal, the change in the detector 2 signal may be used to compensate for the diminished detector 1 signal change. Similarly, when detector 72 is disposed within the beam edge at the outset, a decrease in blood sodium concentration affects both detector signals.

In the lower panel, the result of sodium and flow correction in accordance with the present invention, is shown (solid line), and is compared with the uncorrected signal of through detector 70. Correction is obtained when the detector 2 signal, appropriately amplified, is added to the detector 1. Thus, when corrected, the increase in signal (indicating a decrease in hematocrit) resulting from the addition of 5 ml of normal saline (solid line, NS 5 ml), is about the same as the increase in signal resulting from the addition of 5 ml plasma, as would be expected due to a 5 ml dilution in both cases. In this way, the effect of change in scatter is taken into account to obtain a corrected signal, which may be correlated with hematocrit. This device provides better accuracy (scatter effect completely corrected) and signal to noise ratio. Moreover, change in blood electrolyte concentration, in particular blood sodium concentration, may be determined from the change in scatter.

PREFERRED DEVICE #2

Using a scatter detector as in Preferred Device #1 to take into account the scatter effect, a preferred monitoring device sufficient for determining hematocrit and blood sodium values, may be produced by replacing the three LEDs with a laserdiode that emits an isobestic wavelength. Illustrative is an 814 nm laserdiode available from Spectra Diode Labs. Accordingly, this device may comprise a single isobestic light source and two separate detectors, these being a through detector and a scatter detector. Reference is made to FIG. 4, which illustrates such a device in detail.

When the laserdiode of this preferred device is tuned appropriately to the exact isobestic point, no $SaO_2$ correction is required. Thus, changes in hematocrit may be exclusively related to changes in signal without any need for correcting for $SaO_2$.

The just-described, on-line, monitoring devices are intended for use with a circuit that includes plastic tubing through which a patient's blood is circulated. However, the invention may also be applied to non-invasive devices (probes) similar to those used in $SaO_2$ monitors currently in clinical use. Accordingly, the invention may be embodied in clip-like devices for attachment to body parts which can be transilluminated such as fingers, toes and ear lobes.

In such non-invasive devices, changes in volume and/or emitter-to-detector distance should be minimized. Changes in the light path length cannot be readily differentiated from changes in hematocrit. Similarly, in the earlier-described type of device, a constant light path between a light source, and through and scatter detectors is beneficial. To this end, a generally U-shaped channel may be provided within the device housing and detectors appropriately located along the channel to provide a light path of the same length for directly transmitted and scattered light.

With respect to the non-invasive devices, a tight fit should be ensured. Rotational movement may be prevented by the use of rubberized, high friction surfaces. Changes in volume and device movement may be minimized by tightening with Velcro ® straps. Changes in signal related to temperature change and ambient light leakage may be minimized using DC/AC ratios of pulsed signals, as is commonly done in clinical oxymeters.

In use, a device in accordance with the present invention, may be conventionally calibrated by known standards which produce reference signals equivalent to a wide range of the variables under consideration. In accordance with the present invention, these variables advantageously include hematocrit and sodium values, and as hereinafter indicated, may include values for other optically detectable macromolecules. Suitably, two standards representing high and low ends of each variable under consideration, may be used. Calibration may be at the outset and thereafter as deemed necessary.

When beneficially used for on-line monitoring, hematocrit and the following exemplary, related blood parameters may be followed by a device in accordance with the present invention: transvascular fluid exchange, the adequacy of circulating blood volume, hemoglobin concentration (Hbg), $paO_2$ and arterial oxygen content ($CaO_2$). These measurements are useful in connection with large mammals. Net volume exchange (VE) with or from the circulating vascular volume (VC) at any time (t), may be obtained using hematocrit as a optically detectable reference with the following equation:

$$VE(t) = VC \cdot (1 - Hct_0/Hct(t)),$$

where $Hct_0$ represents the initial hematocrit.

Applications include monitoring of fluid balance. This can be accomplished by continuous calculation of volume exchanged (VE). Monitoring of this parameter is of use in the mobilization of edema because if edema is mobilized into the blood stream, fluid must be removed appropriately to prevent dangerous increases in VC and excessive anemia. In many instances, fluid removal is undertaken in conjunction with acute dialysis, in which case a monitoring device in accordance with the present invention, may be attached to the dialysis circuit. If dialysis is not undertaken, a non-invasive device in accordance with the present invention, may be used.

Applications include assessment of the exchange properties of blood vessels. Normally, transvascular fluid exchange (JV) occurs predominantly around vascular endothelial cells through pathways commonly thought of as "pores". JV is proportional to transvascular pressure gradients (hydrostatic and oncotic) and the total pore cross-sectional area. In turn, oncotic gradients are a function of the vascular-tissue macromolecular concentration gradients, which are determined by the rate of transvascular macromolecular transport and the rate of macromolecular elimination from the tissues.

Transvascular macromolecular transport (JS) may be active or passive. Passive transport is determined by factors including the rate of fluid exchange (JV) carrying the macromolecules through the pores (convection), the interaction between macromolecular size, molecular weight, configuration, deformability and the effective geometry of the pathway (sieving properties), and the macromolecular surface charge in relation to that of the cellular membrane.

In accordance with this application of the present invention, change in membrane characteristics that influence macromolecular transport, including membrane permeability, may be elucidated through analysis of JS by the administration of selected mixtures of appropriate, optically detectable macromolecules in a pharmaceutically acceptable carrier, and use of more than one wavelength. Conveniently, hematocrit may be followed as an optically detectable, reference marker by light of an isobestic wavelength, and it is, of course, therefore important that hematocrit values take into account the scatter effect.

Suitable exogenous macromolecular mixtures include, but are not limited to, fractions of polysaccharides such as fractions of dextrans and hydroxyethylstarch fractions, and fractions of plasma proteins. A suitable macromolecular mixture will include two or more macromolecular components that differ in properties affecting transvascular transport, such as molecular weight, surface charge and rigidity. Generally speaking, the macromolecular components will, for convenience sake, be identical except with respect to the physico-chemical attribute by which they differ. However, as may be understood, the macromolecular components may be two entirely different materials that significantly differ for purposes of this application, only with respect to a property affecting transvascular transport.

A mixture of uncharged and charged macromolecules may be used to elucidate change in vascular membrane charge. It has been hypothesized that change in membrane charge, may be the first step in membrane damage. Thus, elucidation of change in membrane charge may provide an early indication of membrane damage. Sulfated dextrans and diethylaminoethyl dextrans respectively exemplify useful negatively and positively charged exogenous macromolecules.

It is generally accepted that net transvascular fluid exchange occurs through paracellular pores. Macromolecular fractions having a molecular weight of $2 \times 10^4$ or more, are partially restricted as they travel through these pathways. However, smaller molecules (MW less than $2 \times 10^4$) may travel more unimpeded. Therefore, typical macromolecules useful in this application, will have a molecular weight of about $2 \times 10^4$ or more.

To elucidate change in vascular membrane pore size, a macromolecular mixture of components that differ in molecular weight, may be beneficially used. An advantageous molecular fraction may range in molecular weight from about $2 \times 10^4$ to $2 \times 10^6$. A molecular weight greater than about $2 \times 10^6$ is generally considered to be membrane impermeable, and may be used as the reference marker. Generally speaking, as may be understood, the degradation rate of macromolecules is advantageously slow in comparison to the transvascular transport rate.

Active mechanisms have been hypothesized for protein transport, particularly during inflammatory reactions. A measure of the relative importance of active mechanisms may be elucidated from comparisons of JS for specific protein fractions of known molecular weight, charge and physical properties, with JS of the exogenous macromolecules mentioned previously.

As previously indicated, net volume exchange (VE) of fluid with the vascular volume (VC) may be followed from change in concentration of an optically detectable, reference substance or marker (CR) which does not escape the blood vessels, using the following equation:

$$VE(t) = VC \cdot (1 - CR(0)/CR(t)),$$

where $CR(0)$ represents the initial concentration, and $CR(t)$ the concentration of the reference marker at time (t). If the marker is dissolved in plasma, VC represents the plasma volume. Conveniently, hemoglobin (Hbg) or hematocrit (Hct) may be used as the reference substance or marker, and followed by an isobestic wavelength. In such case, $CR(0)$ and $CR(t)$ in the foregoing equation may be replaced by $Hbg(0)$ and $Hbg(t)$, or $Hct(0)$ and $Hct(t)$, respectively.

Net, ongoing transvascular exchange of a mixture of macromolecular markers (JS) may be determined using the following equation for each optically detectable component of the macromolecular mixture, and using a distinct wavelength for each component:

$$MM(t) = CM(t) \cdot (VC - VE(t)),$$

where MM(t) and CM(t) represent the mass and concentration of a particular macromolecular component at any time (t). JS(t) for a particular macromolecule marker at any given time (t), may be computed as the change in mass per unit time using the following equation:

$$JS(t) = \Delta MM/\Delta t,$$

where ΔMM represents the change in mass of a particular macromolecular marker during a period of observation Δt. Simultaneous analysis of JS for each of the components of a macromolecular mixture, allows assessment of vascular membrane change relevant to function and ability to regulate fluid exchange. As may be understood, sufficient time will typically be allowed after administration of an exogenous macromolecular mixture, to permit transvascular transport within the body of the patient of at least a portion of the mixture.

In accordance with a suitable embodiment of this application of the present invention, macromolecules may be labelled with optically detectable markers such as colored dyes, in particular dyes approved for human and veterinary use. In this regard, a first specific fraction of a macromolecule may be labelled with a dye having a certain light absorbance peak, and a second specific fraction of the macromolecule may be labelled with a different dye having a distinct light absorbance peak. Thus, macromolecules having an average molecular weight of 40,000 may be labelled with a dye having a light absorbance peak at 555 nm, and identical macromolecules having an average molecular weight of 500,000 may be labelled with a dye having a light absorbance peak at 670 nm. Conventional methods may be used for covalently bonding suitable dyes to selected macromolecules.

Dyes used to label specific macromolecules are beneficially selected with light absorbance peaks as far apart as possible, within a convenient range of about 300 to 1000 nm, so that light of a distinct wavelength may be selected for each type of optically detectable macromolecule. Thus, as may be understood, red light may be used to follow macromolecules labelled with a blue dye, blue light may be used to follow macromolecules labelled with a red dye, orange light may be used to follow macromolecules labelled with green dye, and so forth.

Naturally occurring dyes such as animal, plant and fruit pigments, may be used for labelling macromolecules. Optical detection, of course, is not limited to the use of dye labels; polarized light and refractive index, for example, may be used to provide for optical detection of suitable macromolecules.

PREFERRED DEVICE #3

Figure 10A:
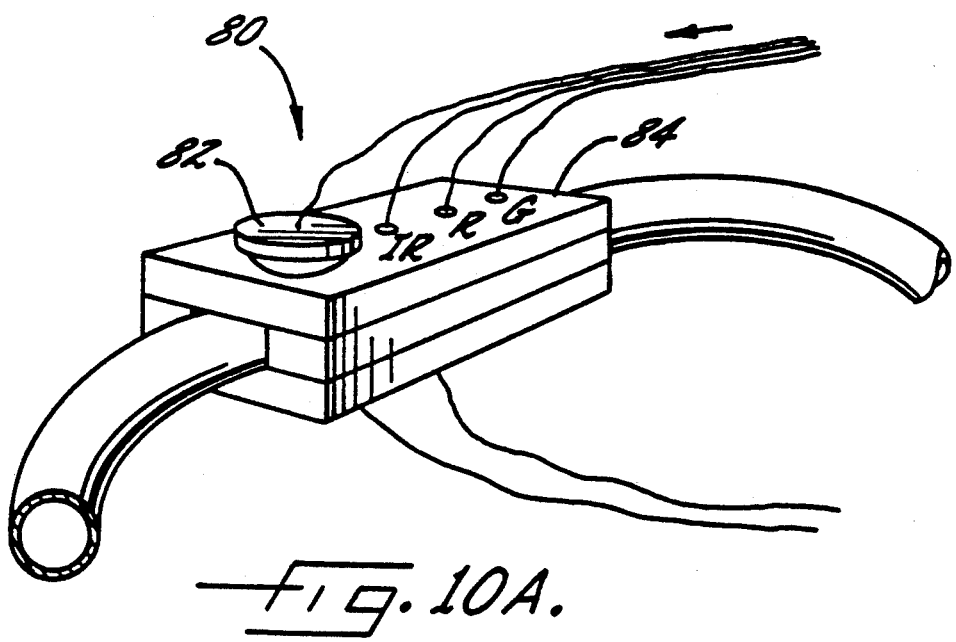
FIGS. 10A-10B illustrates another preferred embodiment of a device in accordance with the present invention, with FIG. 10B being a view similar to FIG. 6C.
Figure 10B:
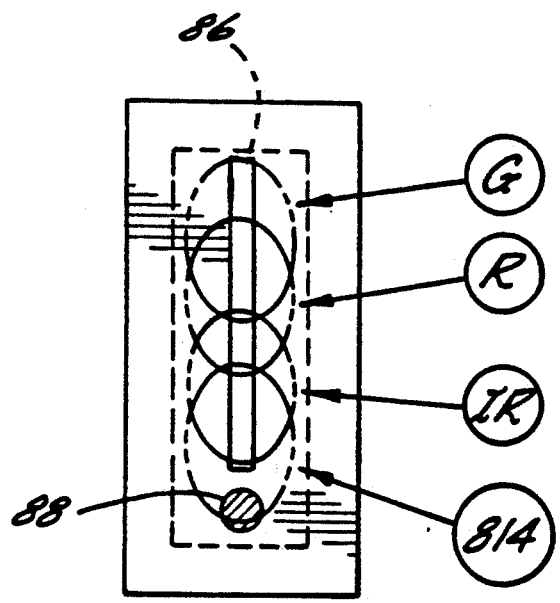

A preferred device 80 for use in this application of the present invention, is depicted in FIG. 10. Multiple wavelengths are used to separate effects due to oxygen saturation and light scatter from transvascular fluid exchange and transvascular molecular transport.

An isobestic wavelength of about 814 nm may be beneficially used to follow change in hematocrit. A laserdiode 82 may be used as the source of this wavelength. Additional distinct wavelengths, for instance, green (G) and red (R) wavelengths, may be used to follow changes in blood concentration of each component of a two component, macromolecular mixture respectively labelled with orange and blue dyes. An additional wavelength greater than 814 nm, for instance, 940 nm (IR), is beneficially used to determine the effect of changes in $SaO_2$ with respect to the signals from the green and red wavelengths. The areas illuminated by the four wavelengths are represented with dashed ellipses. If desired, the light sources may be remotely located from housing 84 of device 80, in which case the light signals may be carried by fiber optic cables.

Proximate to a main photodetector 86, there is an additional photodetector 88 for taking into account the scatter effect with respect to the hematocrit measurement. Pulsed signals are used with respect to the main photodetector. Main photodetector 86 may be shortened and an additional photodetector placed in the optical axis of the light beam from the 814 nm light source. As stated previously, volume exchanged (VE) with or from the circulating vascular volume (VC) at any time (t) may be obtained using hematocrit as the reference marker and the equation:

$$VE(t) = VC \cdot (1 - Hct_0/Hct(t)).$$

Figure 11:
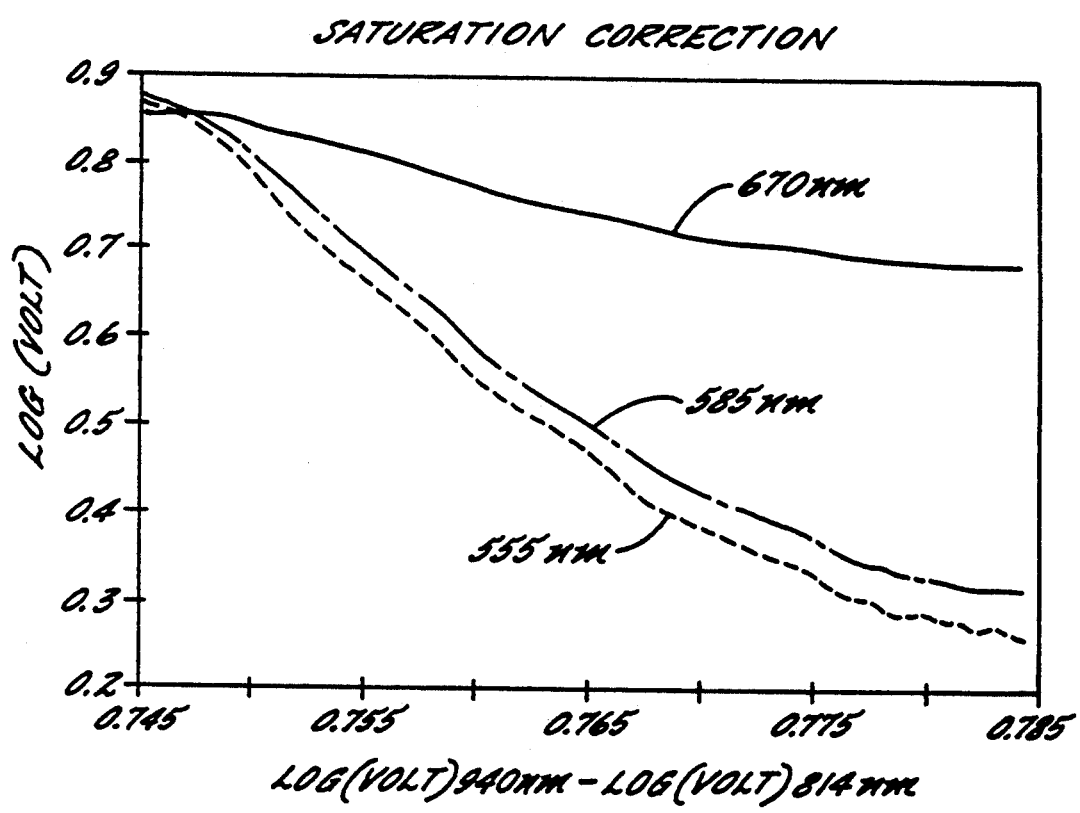
FIG. 11 illustrates another graph correcting for change in oxygen saturation.

JS for each type macromolecule may be isolated from confounding changes by subtracting changes in $SaO_2$ and changes related to the presence of red cells (Hct, sodium and flow effects) from the overall signal change obtained for a particular light wavelength. Thus, by advantageously using an additional infrared light source, that is, 940 nm, the difference between the 940 and 814 nm signals (proportional exclusively to changes in $SaO_2$) may be used to correct the signals from the red and green wavelengths for saturation related changes. In FIG. 11, this difference is illustratively related to changes in 670, 585, and 555 nm light.

Figure 12A:
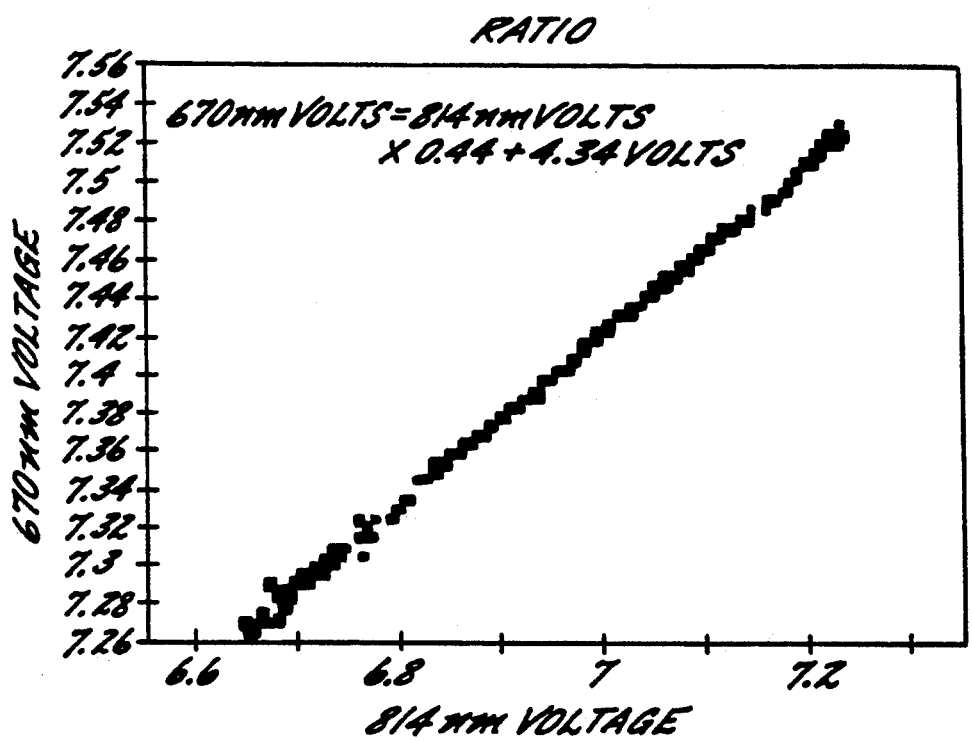
FIGS. 12A-12B illustrate graphs for correcting for the Red Cell Effect.
Figure 12B:
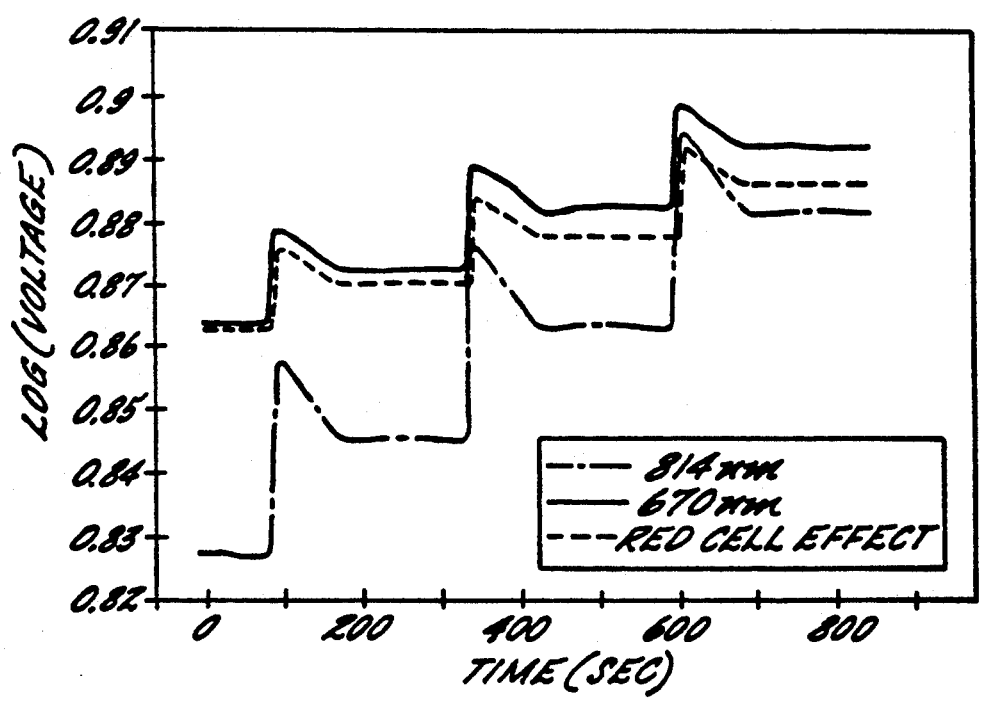

In the upper panel of FIG. 12, red cell related signal changes in 670 nm light (ordinate) are plotted against similar changes in the 814 nm (abscissa) signal, in the absence of optically detectable, exogenous macromolecules. When 814 nm signal changes are multiplied by the Ratio (slope of plot), all red cell related changes (Hct, sodium and flow artifacts) can be subtracted from the signals for the optically detectable macromolecules. In the lower panel of FIG. 12, the red cell related changes (Red Cell Effect) are subtracted from 670 nm signal changes. The difference represents the change in light associated with the change in concentration of the optically detectable macromolecules.

In summary, the change in any specific light may be related to changes in the concentration of optically detectable macromolecules ($\Delta \log(Volt)_{CM}$) as follows:

$$\Delta\log(Volt)_{CM} = \Delta\log(Volt)_{spec.wave} - \Delta\log(Volt)_{814} \cdot Ratio - [\Delta\log(Volt)_{940} - \Delta\log(Volt)_{814}] \cdot SaO_2 factor.$$

Thus, VE and JS for specific macromolecules may be respectively calculated from on-line changes in concentration of hematocrit and optically detectable macromolecules using light of a plurality of distinct wavelengths.

Figure 13A:
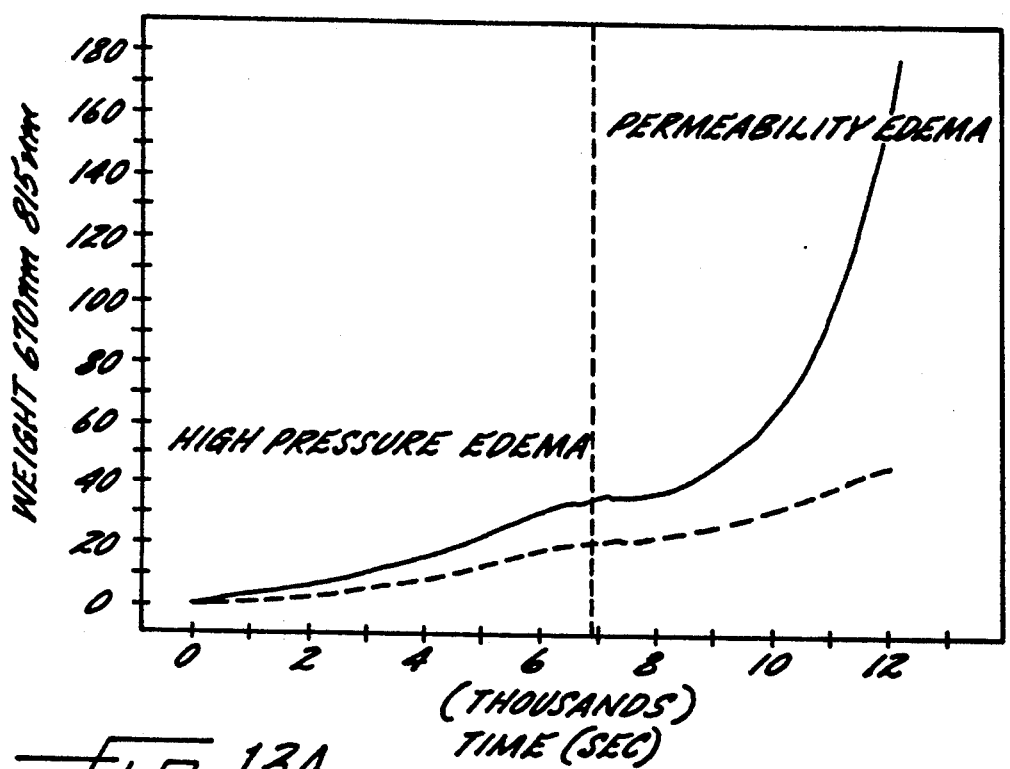
FIGS. 13A-13B show differences in VE relative to red cells and a macromolecular mixture, under high pressure edema and permeability edema conditions.
Figure 13B:
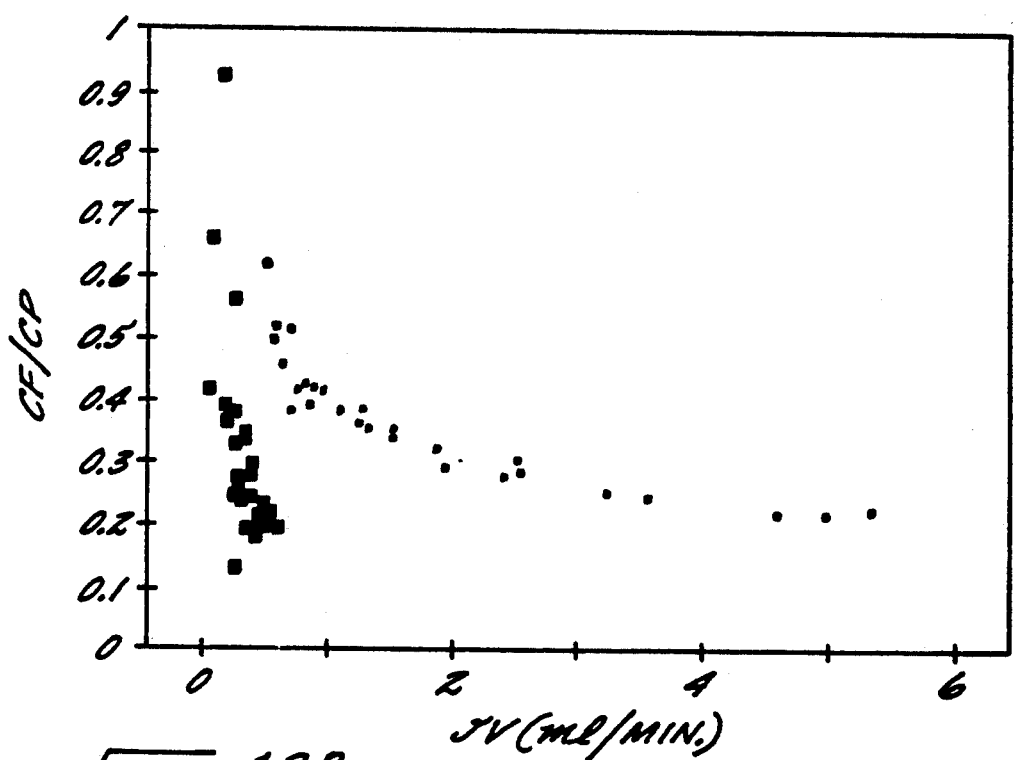

The upper panel of FIG. 13 shows changes in VE relative to red cells and a Reactive Blue labelled mixture of uncharged Dextrans (40D and D500), using isolated excised canine left lower lobes. The solid line shows change in VE relative to red cells, and the dashed line shows change in VE relative to the optically detectable macromolecular mixture. Changes associated with high pressure edema and change in vascular integrity (without change in capillary hydrostatic pressure) induced by the addition of sodium EDTA, are both shown. During high pressure edema the optically detectable macromolecules are concentrated significantly, but concentration of the macromolecules decreases relative to the red cells after the permeability lesion is induced. As may be understood, this type of study differentiates between edema caused by increased hydrostatic pressure and edema caused by increased vascular permeability, and thus may assist in pathophysiological diagnosis, as well as prognosis.

In the lower panel of FIG. 13, the concentration of optically detectable macromolecules in the filtered liquid (indexed for its plasma concentration, CF/CP), is plotted against the rate of transvascular fluid exchange (JV), to express membrane selectivity. An ideal selectivity would be 1 (100%), which would result in CF/CP=0. The values obtained during high pressure edema (squares), approach this ideal to a greater degree than the values obtained after permeability changes (dots).

Once transport-affecting properties of a vascular membrane have been evaluated, specific therapeutic interventions may be commenced. To this end, a suitable therapeutic agent may be administered in a pharmaceutically acceptable carrier, in an amount sufficient to assist fluid removal. If the therapeutic agent is for restoring membrane permeability, an evaluation such as illustrated in FIG. 13, may assess drug efficacy. Alternatively, edema reabsorption may be induced by changes in pulmonary capillary pressure and/or plasma oncotic pressure, and the edema reabsorption may be monitored by monitoring VE as previously discussed. To this end, colloid osmotic agents as exemplified in Landolfo and Oppenheimer, "Resolution of Low Pressure Pulmonary Edema with an Osmotic Agent," Abstract, *Am. Rev. Resp. Dis.* 141: A296 (1990), may be administered at a therapeutically effective dosage level capable of modifying the oncotic gradient. The information obtained may be also useful in selecting effective macromolecular agents for assisting fluid removal and appropriate dosage. Properties to be considered include size, charge and rigidity of macromolecules.

Applications of the present invention further include monitoring of fluid balance with appropriate feedback. When a monitoring device in accordance with the present invention, is placed on a dialysis/CAVH system, proximal to the filtering device, a patient's hematocrit and the volume exchanged from the patient's blood volume may be continuously monitored and displayed. This information may support a feed-back electronic system to regulate the rate of ultrafiltration (QF) and to maintain an adequate and safe circulating blood volume while fluid exchange is induced.

QF is determined by the balance between transmembrane hydrostatic pressure gradient (TMP) and oncotic forces. For example, TMP may be set to induce a VE of about 10% of VC in 20 min., at which point QF may be decreased automatically by the feed-back system to allow fluid mobilization from the tissues. Once VE decreases to 7.5% of VC, QF may be resumed. In this way, QF may be adjusted automatically to predetermined VE considered safe. In addition, in the event of desaturation (likely associated with decreased cardiac output even before a change in blood pressure is detectable), the feed-back system may be set to decrease QF and, in dialysis machines, where blood flow through the filtering/exchanging device (QB) is controlled by a roller pump, to also decrease QB.

When an additional monitoring device in accordance with the present invention, is placed in dialysis outflow tubing, outflow hematocrit may also be monitored. This information may be of value in detecting excessive hemoconcentration, which may not only increase blood viscosity and clotting problems in the dialysis device, but also may result in increase in protein oncotic forces which may require high TMP to induce ultrafiltration. High TMP may damage the dialysis device. To prevent this problem, the feed-back system could increase QB and decrease QF until the outflow hematocrit returns to an acceptable level.

Figure 14:
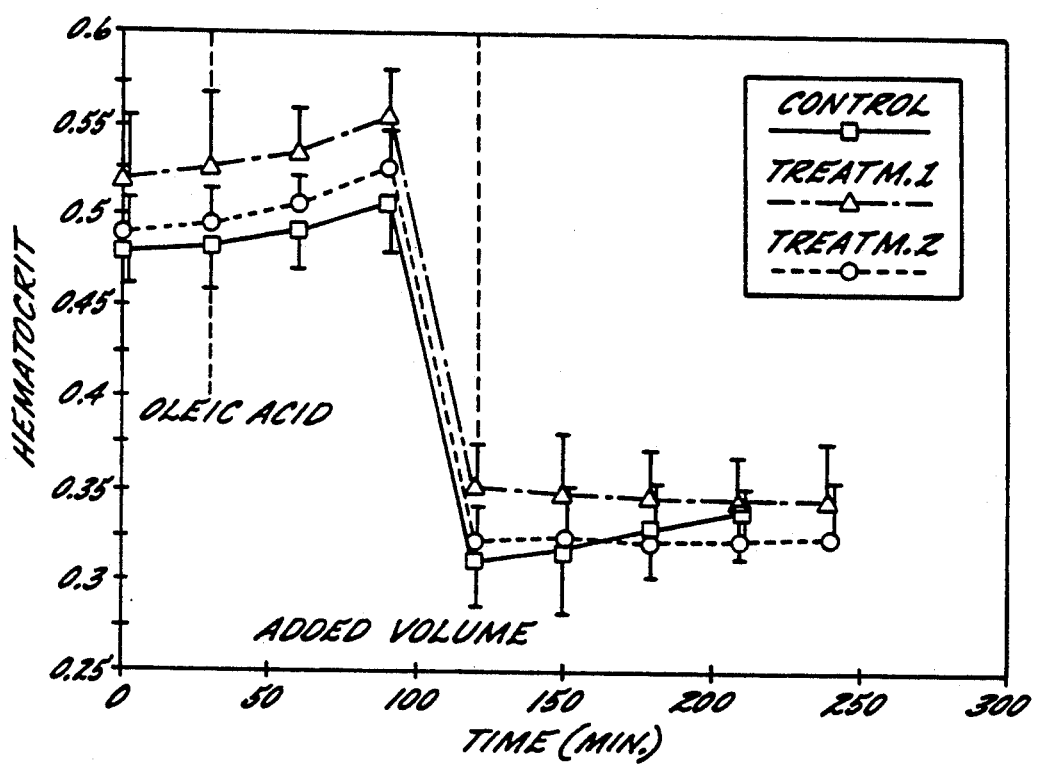
FIGS. 14-16 respectively show the time courses of on-line hematocrit, volume of lobar edema and COP, for a study in which a therapeutic agent is administered and rate of fluid removal is regulated.
Figure 15:
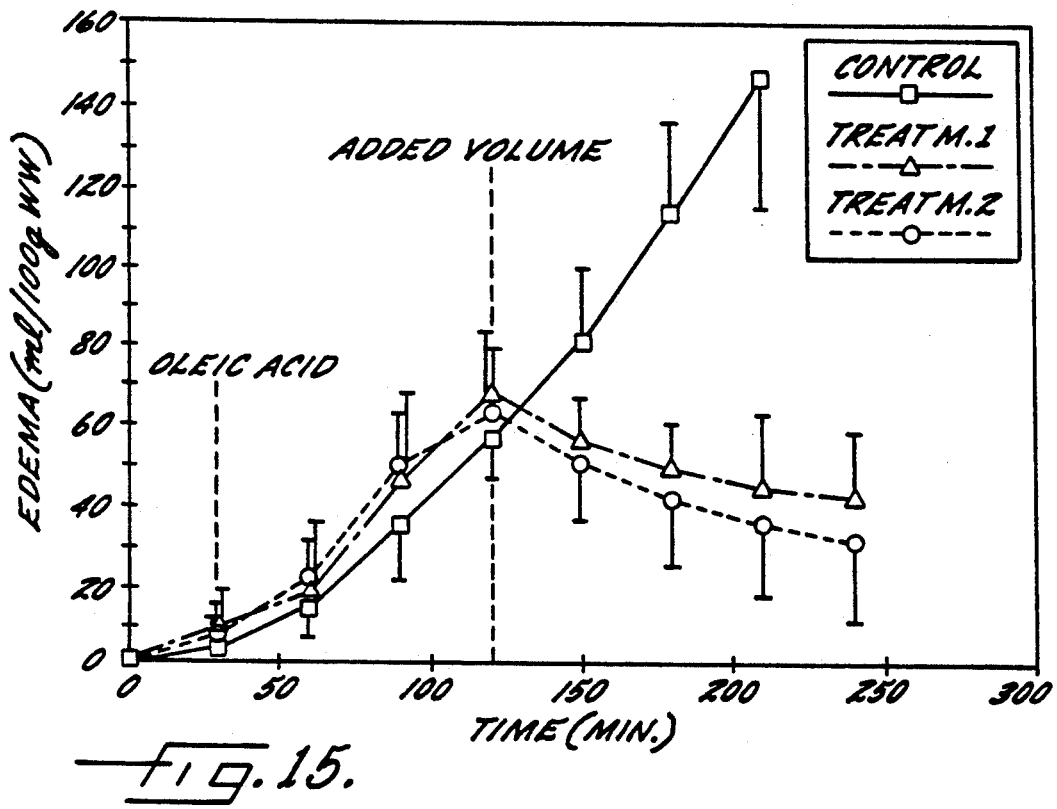
Figure 16:
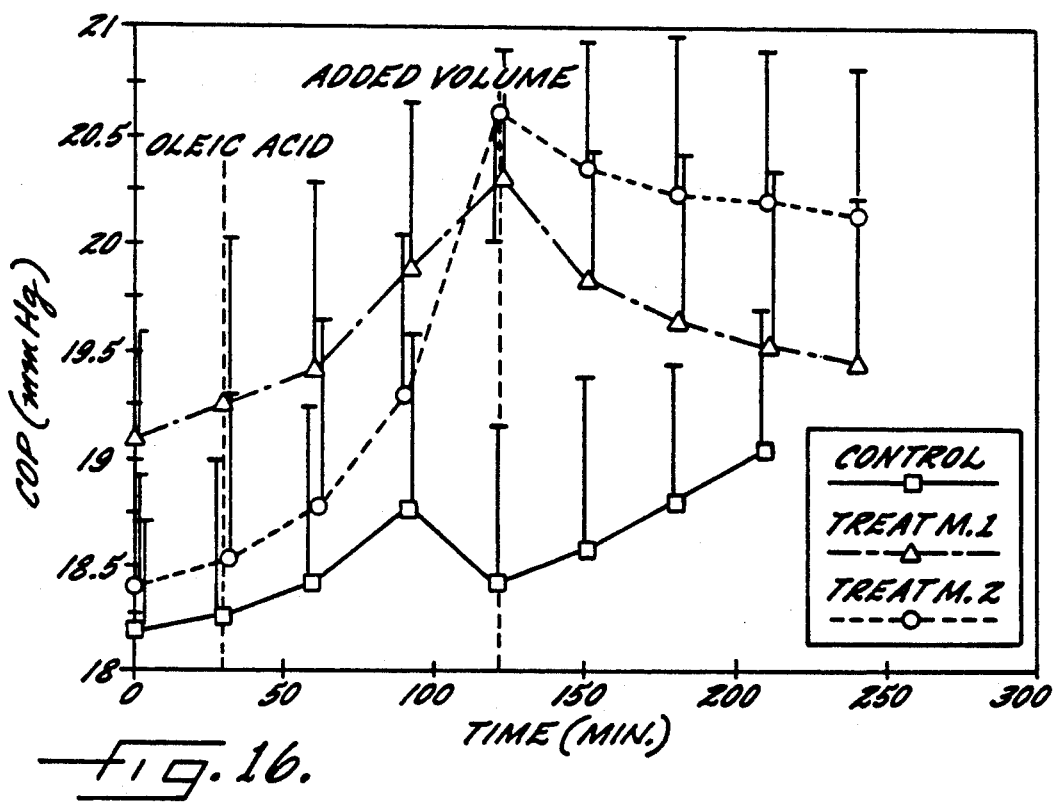

Monitoring fluid balance and using feedback to regulate ultrafiltration, is now further exemplified with respect to administration of an edema reabsorption-inducing macromolecular agent, and by the data of FIGS. 14–16. The evaluation is carried out using eighteen isolated, blood perfused, canine left lower lobes.

A hematocrit monitoring device is placed into the perfusion circuit and calibrated using microhematocrit values determined with a centrifuge. Continuous determination of lobar weight is provided for. The lobes are kept at a transpulmonary pressure of 3 cm $H_2O$. Arterial, venous and airway cannulae are provided with small diameter catheters for hydrostatic pressure measurement. Signals proportional to hydrostatic pressure, weight and hematocrit are recorded. Plasma colloid osmotic pressure (COP) is determined using a Wescor Colloid Osmometer, using a membrane restricting the exchange of macromolecules of MW=30,000 or higher.

After blood flow is re-established, the venous reservoir is manipulated to ensure a pulmonary capillary pressure of 12 cm $H_2O$. After a period of stabilization of approximately 30 minutes, COP and hematocrit are determined.

Thereafter, 0.15 ml of oleic acid suspended in TWEEN is slowly infused (approximately 3 minutes) into the arterial line. The dose is small so as to induce only moderate changes in capillary permeability. Weights and on-line hematocrits are continuously observed until a new steady state as indicated by a constant rate of filtration, is observed, at which time blood measurements are repeated.

Six lobes serve as a control. To control for the potential effects of decreasing hematocrit, these lobes are treated with 250 ml of plasma and observed for two additional hours. At half hourly intervals, COP and hematocrit are determined.

The remaining twelve lobes receive 250 ml of 6% hydroxyethylstarch (HES) solution, so as to be treated to a final concentration of 2.7%. HES is an uncharged polydisperse starch solution having a wide molecular weight range, in which molecular weight varies from ten thousand to two million with an average molecular weight of 450,000. The HES is added over a period of 30 minutes after which COP and hematocrit measurements are repeated.

The treated lobes are subdivided into two equal groups of six lobes each, termed Treatment 1 group and Treatment 2 group. The time course of both weight and on-line hematocrit is followed for two hours. In the Treatment 2 group, to minimize autodilution of HES, hematocrit is maintained constant by continuous ultrafiltration using a pediatric hemofilter in the perfusion circuit. COP and hematocrit are determined every 30 min.

At the end of the evaluation, lobar wet weight is obtained by subtracting the weight of the cannulae, and the lobes are dried to a constant weight in an oven at 80° C. The data is statistically evaluated as follows: paired Student t tests are used to evaluate changes within groups, and for inter group comparisons, analysis of variance is applied. Results are summarized in FIGS. 14-16. The bars represent standard deviations.

With reference to FIG. 14, hematocrits initially increase, indicating loss of perfusate into lobes. Decrease in hematocrit is observed when plasma (Control) or hydroxyethylstarch is added. In the Treatment 1 group, there is a gradual decrease in hematocrit due to edema reabsorption; whereas in the Treatment 2 group, ultrafiltration maintains the hematocrit constant.

In FIG. 15, the volume of lobar edema, normalized to 100 grams of initial wet weight, is plotted against time. Acceleration in the rate of edema after the addition of oleic acid, indicates significant lesions are produced. Both treated groups show reduction in edema after the administration of HES. There is, however, a gradual decrease in the rate of reabsorption. Ultrafiltration results in additional edema reduction (about 10%) in the lobes of Treatment 2 group; however, no statistical difference is found.

With reference to FIG. 16, COP initially increases in all groups, reflecting fluid loss due to edema accumulation. The addition of HES significantly increases COP in both treated groups; however, COP decreases with time. In the Treatment 1 group, this decrease may be the result of autodilution and/or loss of HES. The confounding effect of hemodilution is eliminated in the Treatment 2 group.

Applications of the present invention include determination of blood concentration of additional hemoglobin species. To this end, an isobestic wavelength may be used to determine hematocrit, and additional wavelengths appropriate for optical detection of these species including carboxyhemoglobin and methemoglobin, may be used.

The present invention may also provide an estimate of arterial blood oxygen content ($CaO_2$), which provides an index of oxygen carrying capacity. $CaO_2$ may be calculated as follows: First, hematocrit may be converted to Hbg (g/dL) assuming a normal mean corpuscular hemoglobin concentration (MCHC), using the equation: $Hgb = Hct(\%) \cdot 3.39$ g/dL. Then, $pO_2$ may be estimated from blood saturation changes using the oxygen dissociation curve in form of a look-up table. $CaO_2$ may be obtained as follows:

$$CaO_2(ml/dL) = Hbg(g/dL) \cdot Saturation(\%) \cdot 1.36(ml/g) + pO_2 \cdot 0.003(ml/mmHg/dL).$$

Low $CaO_2$ is incompatible with adequate tissue oxygenation even when blood pressure is normalized.

Having described the invention in detail and by reference to preferred embodiments, it will be apparent that modifications and variations are possible without departing from the scope of the invention defined in the appended claims. Several variants or modifications have been briefly mentioned for purposes of illustration.

I claim:

1. A method for optically determining blood parameters, said method comprising directing a light beam into a patient's blood, detecting and measuring the light emerging from the blood, and compensating for any change in light beam geometry induced by any change in blood electrolyte composition.

2. The method of claim 1, wherein blood concentration of endogenous, optically detectable macromolecules is determined.

3. The method of claim 1, comprising eliminating the effect of blood oxygen saturation on said determination, wherein hematocrit is determined.

4. The method of claim 3, wherein an isobestic wavelength is selected.

5. The method of claim 1, further comprising directing into the blood, light of a wavelength selected to detect optically detectable macromolecules, and detecting emerging light of said wavelength.

6. The method of claim 1, wherein said electrolyte is sodium.

7. The method of claim 1, wherein said light beam is directed into an extracorporeal circuit containing flowing blood.

8. The method of claim 7, comprising returning the blood to the patient after said detecting step.

9. The method of claim 1, wherein detected changes in fluid balance are monitored to achieve fluid level management.

10. The method of claim 9, wherein in conjunction with said monitoring to achieve fluid level management, rate of fluid removal is regulated.

11. The method of claim 10, further comprising administering to the patient, a suitable therapeutic agent in an amount sufficient to assist fluid removal.

12. The method of claim 1, wherein blood oxygen content is determined.

13. The method of claim 1, comprising prior to said light detecting step, determining light beam geometry and selecting detectors located for sensitivity to change in light beam geometry.

14. A method for optically determining the blood concentration of macromolecules useful in evaluating exchange properties of blood vessels of a patient, comprising adding to the blood of the patient, a macromolecular mixture comprising a first macromolecular component characterized by a first vascular transport-affecting property and a first optically detectable property, and a second macromolecular component characterized by a second vascular transport-affecting property and a second optically detectable property, wherein said first and second transport-affecting properties differently affect transvascular transport, and wherein said first optically detectable property is optically distinct from said second optically detectable property; and optically detecting change in blood concentration of at least one component of said macromolecular mixture, using a wavelength appropriate for each component determined.

15. The method of claim 14, wherein change in blood concentration of said first macromolecular component and of said second macromolecular component of said macromolecular mixture is optically detected, using a first wavelength appropriate for said first optically detectable property, and a second wavelength distinct from said first wavelength and appropriate for said second optically detectable property.

16. The method of claim 14, wherein said transvascular transport-affecting properties are selected from the group consisting of molecular weight, charge and rigidity.

17. A method for optically determining blood sodium concentration, said method comprising directing a light beam into a patient's blood, detecting and measuring the light emerging from the blood, and evaluating any change in scatter of said light beam by comparison to a sodium reference, whereby an absolute blood sodium concentration may be obtained.

18. A device for optically determining blood parameters, said device comprising means for generating a light beam suitable for being directed into a patient's blood; first detecting means and second detecting means each disposed at a suitable location to be sensitive to any change in scatter of said light beam, but differently disposed with respect to said light beam; sodium concentration reference means; and signal evaluation means in operative communication with said first detecting means, said second detecting means, and said sodium concentration reference means.

19. The device of claim 18, wherein said detecting means are light detecting means, and wherein said location for said first detecting means provides for directly emerging light to be predominantly detected.

20. The device of claim 18, wherein a constant light path length is provided.

21. The device of claim 18, wherein said means for generating a light beam, emits an isobestic wavelength.

* * * * *